(12) United States Patent
Elyan et al.

(10) Patent No.: US 7,162,007 B2
(45) Date of Patent: Jan. 9, 2007

(54) NON-INTRUSIVE INSPECTION SYSTEMS FOR LARGE CONTAINER SCREENING AND INSPECTION

(76) Inventors: Vladimir V. Elyan, 45-56, Bolschaya Gruzinskaya str., Moscow (RU) 123056; Boris V. Bekhtev, 52-8, Verkhnie Polya str., Moscow (RU) 109369; Gary F. Bowser, 2702 CR 68, Auburn, IN (US) 48706; Sergei Grishin, Proletarskaya 1/2 apt. 61 Zheleznodorozhny, Moscow Oblast (RU); Mark A. Ferderer, 2734 Sterling Manor Dr., Buford, GA (US) 30518; Donatas Masilionis, Savanoriu 302-18, Kaunas (LT) LT3000; Boris S. Sychev, 84-11, Millionstchikova str., Moscow (RU) 115487; Vitaly A. Uvarov, 105-40/3, Veyernaya str., Moscow (RU) 119501

(*) Notice: Subject to any disclaimer, the term of this patent is extended or adjusted under 35 U.S.C. 154(b) by 58 days.

(21) Appl. No.: 11/052,600

(22) Filed: Feb. 7, 2005

(65) Prior Publication Data

US 2006/0008052 A1    Jan. 12, 2006

Related U.S. Application Data

(60) Provisional application No. 60/542,567, filed on Feb. 6, 2004.

(51) Int. Cl.
*G01N 23/04* (2006.01)
(52) U.S. Cl. .................... 378/57; 378/145
(58) Field of Classification Search ........ 378/145–146, 378/64–65, 57, 134, 137–138, 5
See application file for complete search history.

(56) References Cited

U.S. PATENT DOCUMENTS

| | | | | |
|---|---|---|---|---|
| 6,445,766 | B1* | 9/2002 | Whitham | 378/65 |
| 6,459,761 | B1* | 10/2002 | Grodzins et al. | 378/57 |
| 6,542,574 | B1* | 4/2003 | Grodzins | 378/57 |
| 6,628,745 | B1* | 9/2003 | Annis et al. | 378/21 |

* cited by examiner

*Primary Examiner*—Edward J. Glick
*Assistant Examiner*—Hoon Song
(74) *Attorney, Agent, or Firm*—R. Stevan Coursey; Coursey & Coursey, PC

(57) ABSTRACT

Non-intrusive inspection systems, including apparatuses and methods, for non-intrusively inspecting cargo containers employed, generally, in the cargo transportation industry. The non intrusive inspection systems utilize one or more, single or multi-energy electron accelerators arranged in a plurality of different arrangements and orientations to provide two and, essentially, three dimensional views of the contents of (i.e., objects within) a cargo container and to enable discrimination and identification of materials present within the contents thereof.

30 Claims, 11 Drawing Sheets

FIG. 2
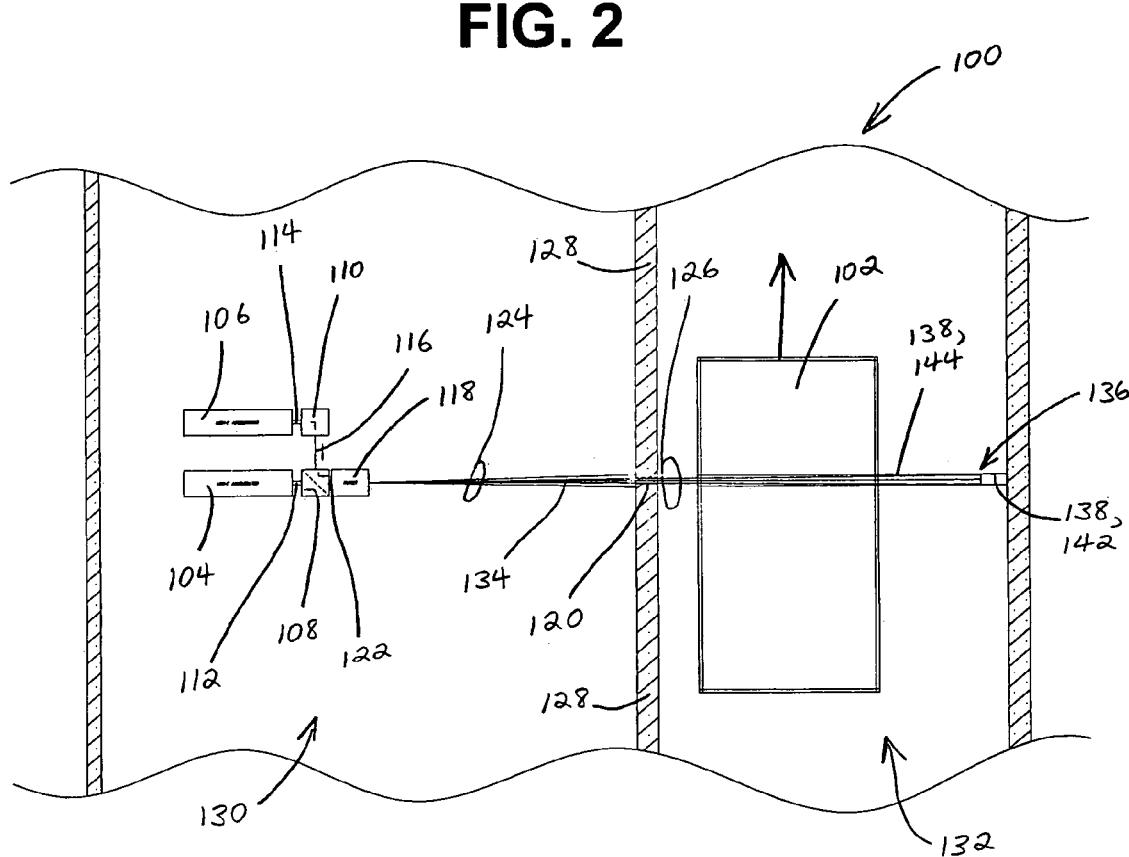
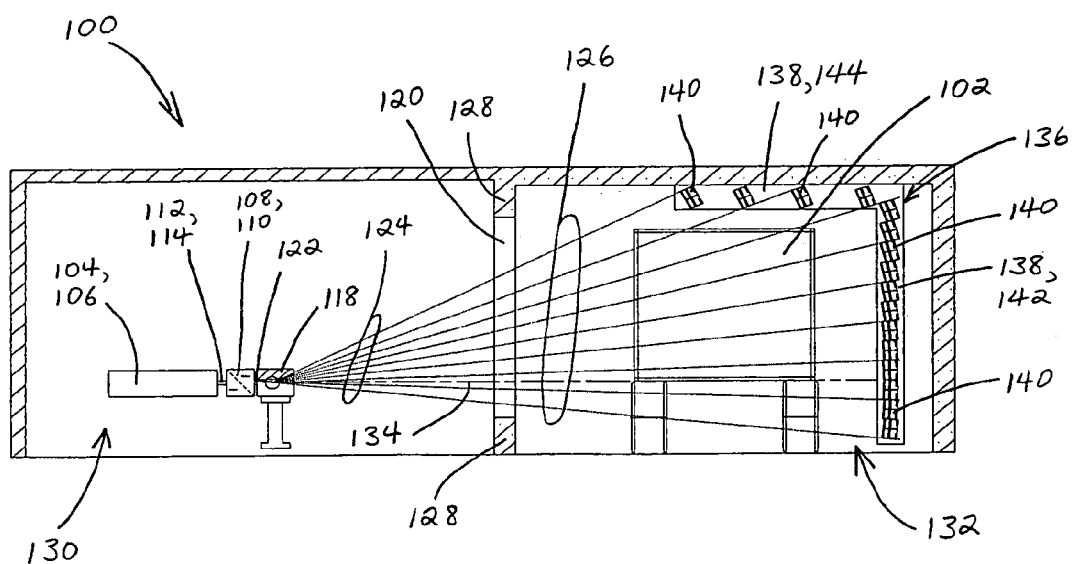
FIG. 1

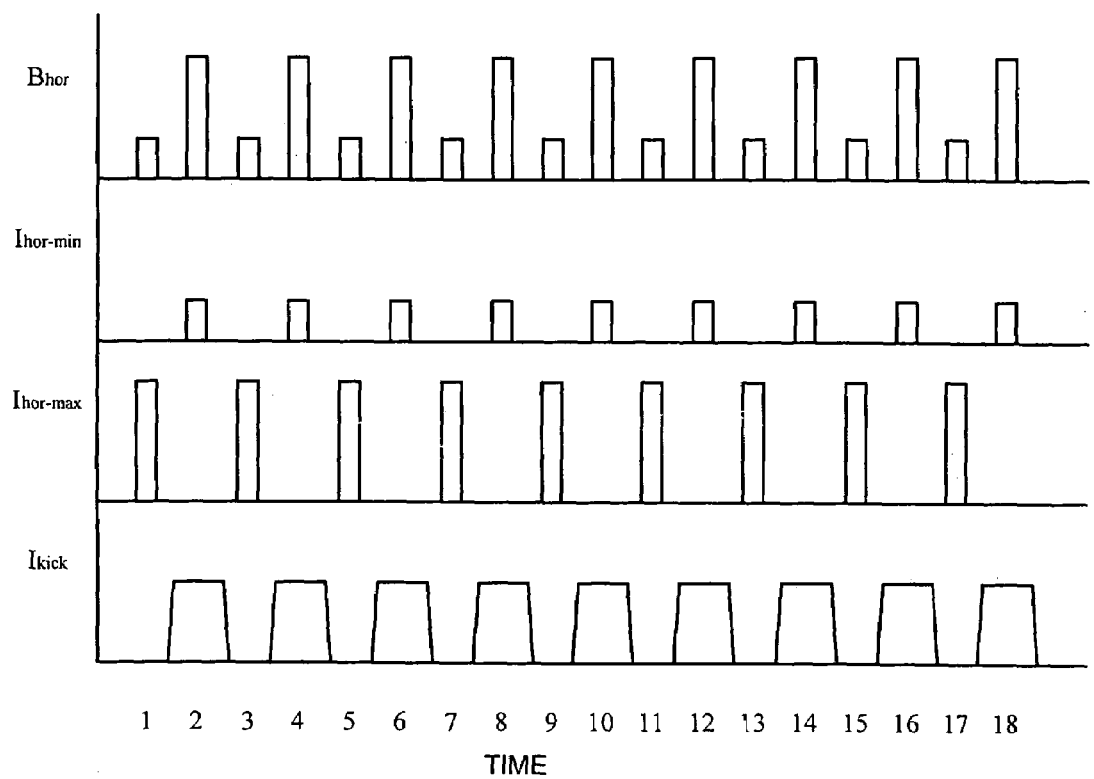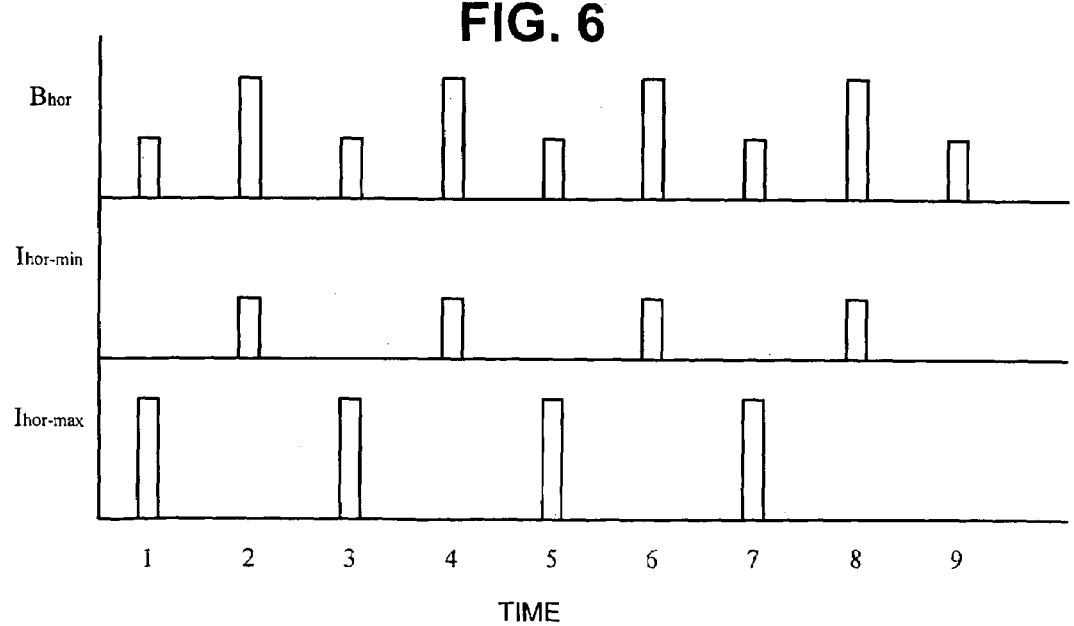

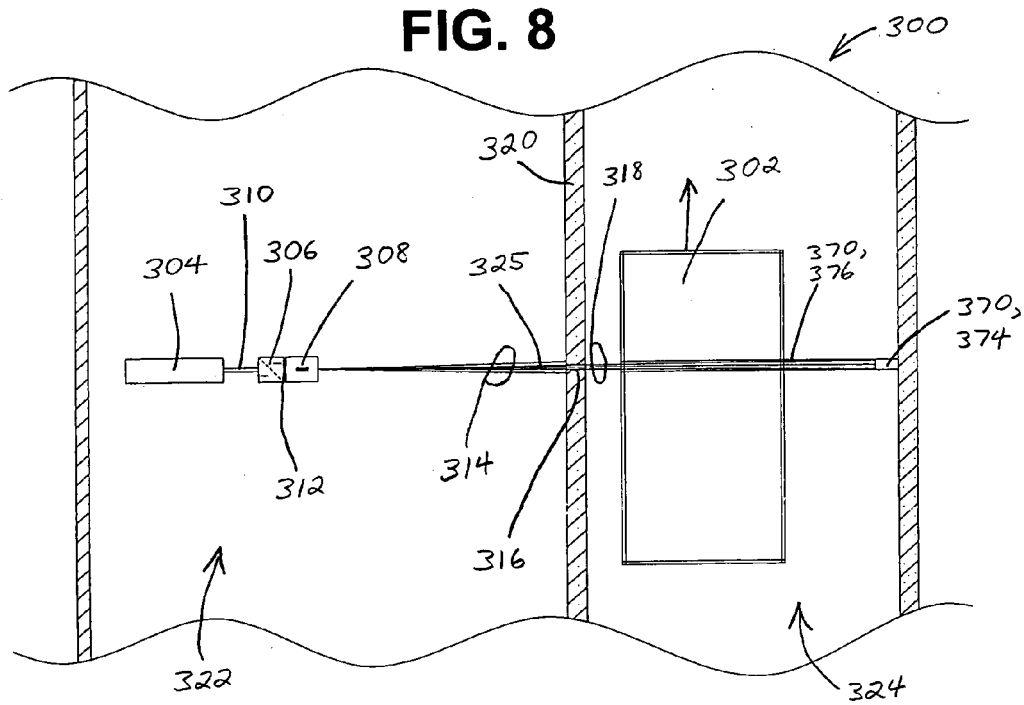
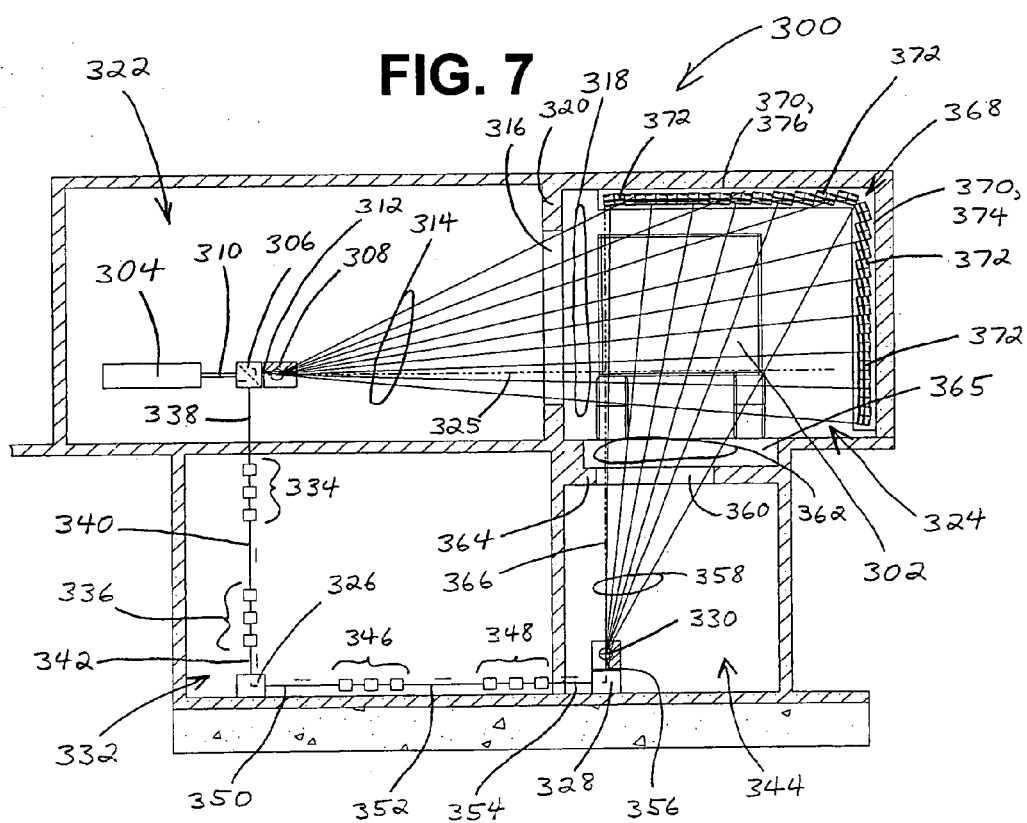

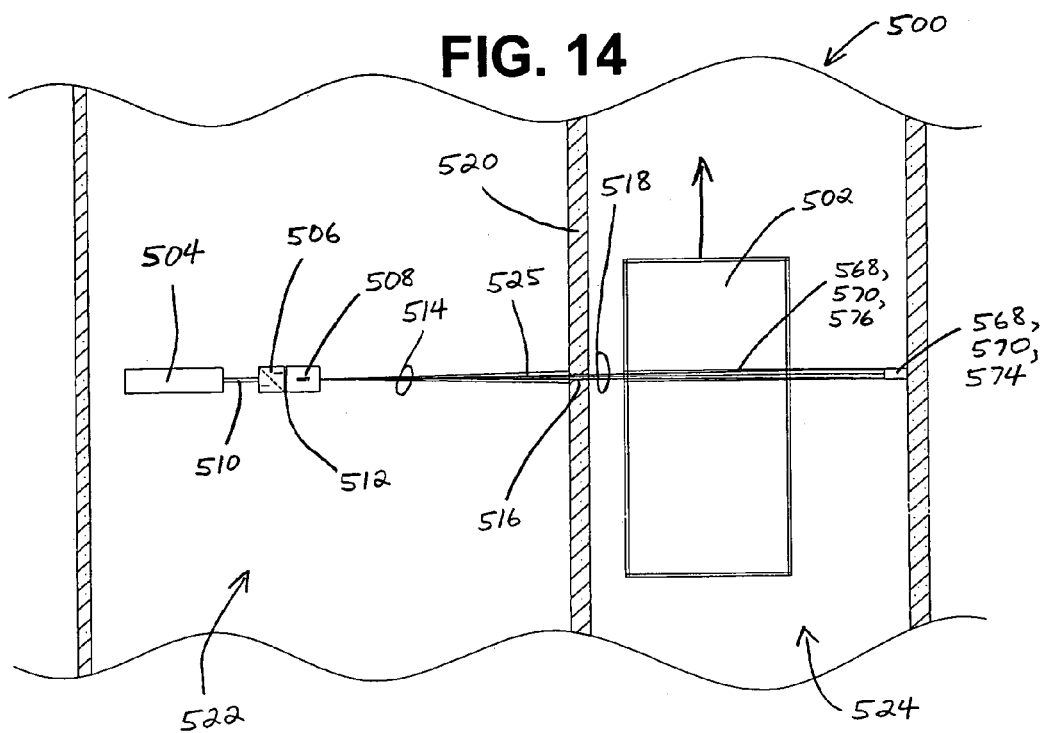
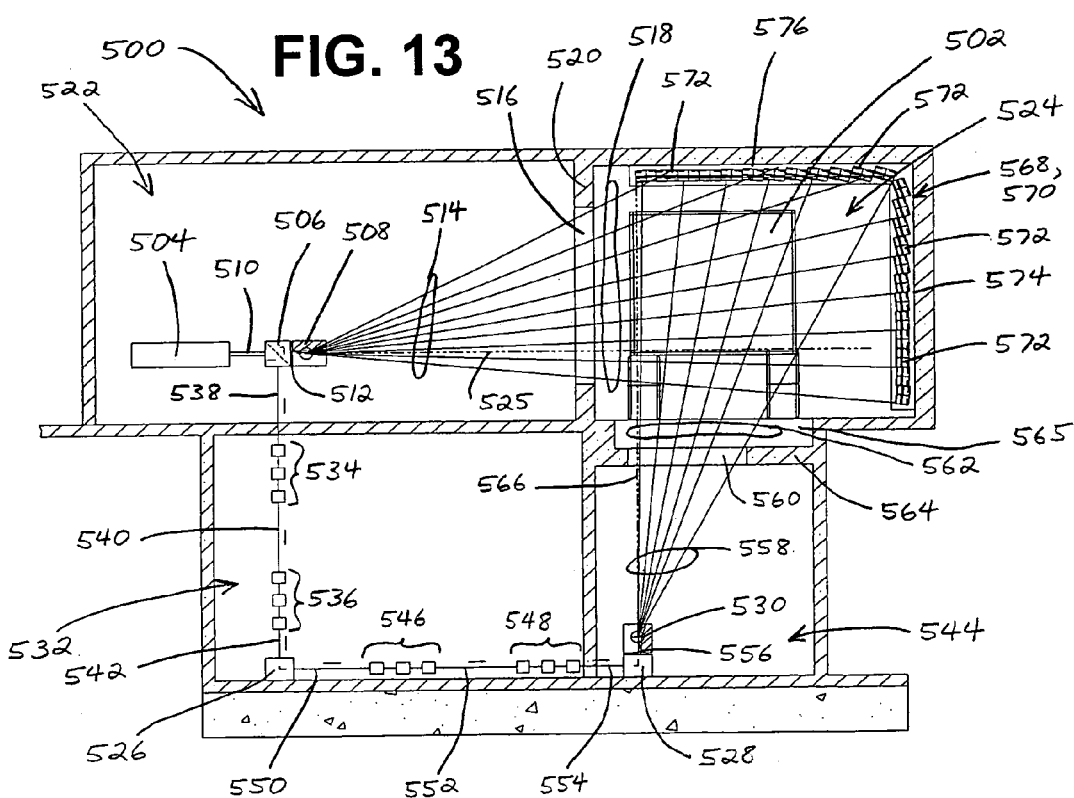

NON-INTRUSIVE INSPECTION SYSTEMS FOR LARGE CONTAINER SCREENING AND INSPECTION

FIELD OF THE INVENTION

The present invention relates, generally, to the field of non-intrusive inspection systems and, more specifically, to non-intrusive inspection systems and methods for inspecting large cargo containers employed, generally, in the cargo transportation industry.

BACKGROUND OF THE INVENTION

Today, due to recent terrorist activities, there is a great concern that terrorists may place explosives, weapons of mass destruction, or other harmful materials in cargo containers that are employed by the cargo transportation industry to ship goods in, for instance, transoceanic commerce. Some vendors have developed non-intrusive inspection systems for such cargo containers that are based upon technology employed in airport baggage scanning systems. Unfortunately, such non-intrusive inspection systems suffer from many difficulties, including that many of the systems do not produce multiple views of the objects present in a cargo container from multiple directions. Further, many of the systems do not provide for the discrimination or identification of materials found in objects present in a cargo container, thereby making the detection of explosives, weapons of mass destruction, or other harmful materials extremely difficult for such systems.

Therefore, there exists in the industry, a need for non-intrusive inspection systems, including apparatuses and methods, for non-intrusively inspecting cargo containers that enable viewing of the contents of such cargo containers in multiple views or planes, enable the discrimination and identification of the materials of objects present in the cargo containers, and that addresses these and other problems or difficulties which exist now or in the future.

SUMMARY OF THE INVENTION

Broadly described, the present invention comprises non-intrusive inspection systems, including apparatuses and methods, for non-intrusively inspecting cargo, containers employed, generally, in the cargo transportation industry. More particularly, the present invention comprises non-intrusive inspection systems, including apparatuses and methods, for non-intrusively inspecting cargo containers utilizing one or more electron accelerators arranged in a plurality of different arrangements and orientations. The non-intrusive inspection systems include systems which utilize one or more, single or multi-energy electron accelerators and that provide multi-dimensional views of the contents of (i.e., objects within) a cargo container and that may, depending on the precise configuration of an embodiment, enable discrimination and identification of materials present within such contents.

Advantageously, the non-intrusive inspection systems of the present invention enable the screening of cargo containers for the presence of particular objects therein without requiring inspection personnel to open the cargo containers and perform physical inspections thereof. Some of the non-intrusive inspection systems of the present invention provide images of the objects present in a cargo container in a single viewing plane, while other non-intrusive inspection systems of the present invention provide images of the objects present in a cargo container in multiple viewing planes (thereby, providing three-dimensional views of the objects). The non-intrusive inspection systems that produce electron beams having electron beam current pulses with multiple energy levels, through use of one or more accelerators, are also capable of discriminating and identifying the materials of objects present in a cargo container.

Further, some of the non-intrusive inspection systems of the present invention may reduce the costs required to obtain similar inspection capabilities. For example and not limitation, a first non-intrusive inspection system may employ two electron accelerators to provide images of the objects of a cargo container in two viewing planes, while a second non-intrusive inspection system that provides images in two viewing planes may employ a single electron accelerator and a plurality of turning, or kicker, magnets to direct electron beam current pulses from the single electron accelerator toward different conversion targets for the generation of bremsstrahlung, or x-rays, that impinge upon a large cargo container from different directions. By eliminating the need for a second electron accelerator and all of the ancillary equipment and containment structures associated therewith, the second non-intrusive inspection system has a lower cost than the first non-intrusive inspection system.

Other advantages and benefits of the present invention will become apparent upon reading and understanding the present specification when taken in conjunction with the appended drawings.

BRIEF DESCRIPTION OF THE DRAWINGS

FIG. 1 displays a side elevation, schematic sectional view of a non-intrusive inspection system for inspecting the contents of a cargo container in accordance with a first exemplary embodiment of the present invention.

FIG. 2 displays a top plan, schematic sectional view of the non-intrusive inspection system of FIG. 1 in accordance with the first exemplary embodiment of the present invention.

FIG. 3 displays a timing diagram illustrating the timing of various pulses during operation of the non-intrusive inspection system of FIG. 1 in accordance with the first exemplary embodiment of the present invention.

FIG. 6 displays a timing diagram illustrating the timing of various pulses during operation of the non-intrusive inspection system of FIG. 4 in accordance with the second exemplary embodiment of the present invention.

FIG. 7 displays a side elevation, schematic sectional view of a non-intrusive inspection system for inspecting the contents of a cargo container in accordance with a third exemplary embodiment of the present invention.

FIG. 8 displays a top plan, schematic sectional view of the non-intrusive inspection system of FIG. 7 in accordance with the third exemplary embodiment of the present invention.

FIG. 13 displays a side elevation, schematic sectional view of a non-intrusive inspection system for inspecting the contents of a cargo container in accordance with a fifth exemplary embodiment of the present invention.

FIG. 14 displays a top plan, schematic sectional view of the non-intrusive inspection system of FIG. 13 in accordance with the fifth exemplary embodiment of the present invention.

DETAILED DESCRIPTION OF THE DRAWINGS

Figure 5:
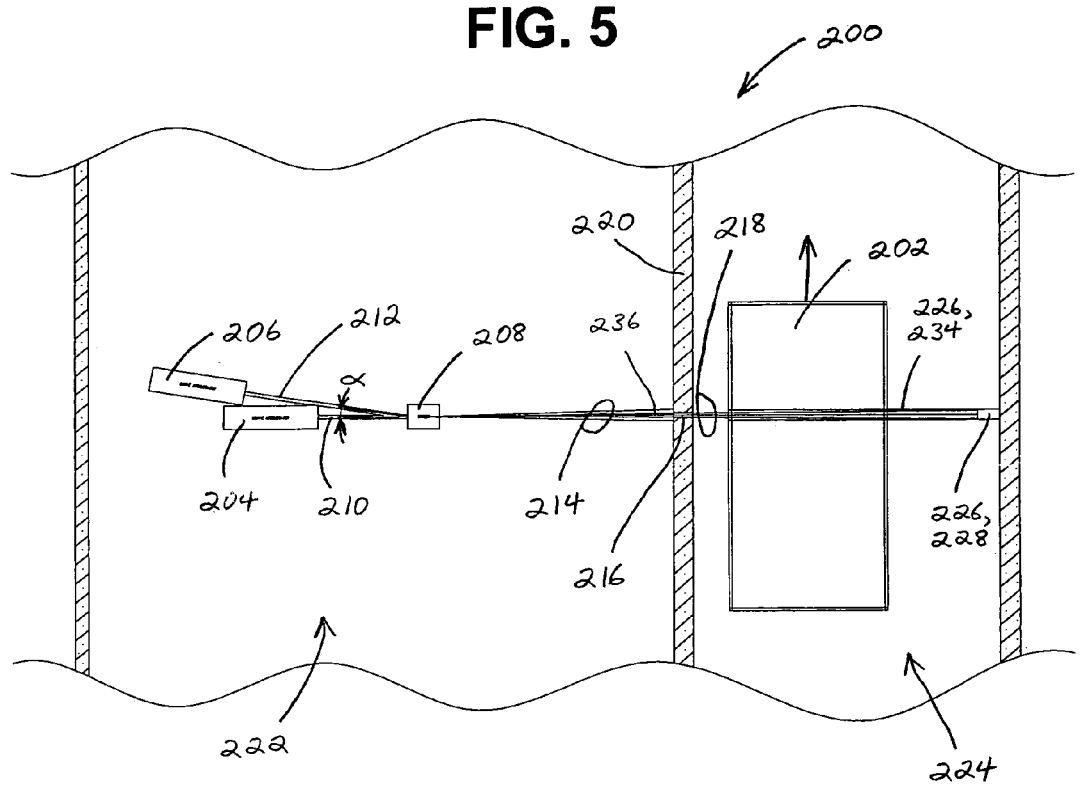
FIG. 5 displays a top plan, schematic sectional view of the non-intrusive inspection system of FIG. 4 in accordance with the second exemplary embodiment of the present invention.

Referring now to the drawings in which like numerals represent like elements or steps throughout the several views, FIG. 1 displays a side elevation, schematic sectional view of a non-intrusive inspection system 100 for inspecting the contents of a cargo container 102 in accordance with a first exemplary embodiment of the present invention. The non-intrusive inspection system 100 comprises first and second accelerators 104, 106 and first and second turning magnets 108, 110 (also sometimes referred to herein as "kicker magnets 108, 110). The first accelerator 104 comprises a pulse-type, electron accelerator that is operable to produce, or emit, a pulsed beam of accelerated electrons including a plurality of electron pulses having a first energy level and traveling in a first direction. The second accelerator 106 comprises a pulse-type, electron accelerator that is operable to produce, or emit, a pulsed beam of accelerated electrons including a plurality of electron pulses having a second energy level and traveling in a second direction. The first and second energy levels are, generally, different. The first and second directions are also, generally, different.

The first and second turning magnets 108, 110 are connected, respectively, to the output ports of the first and second accelerators 104, 106 by vacuum electron beam guides 112, 114 which are adapted to guide respective pulsed beams of accelerated electrons from the output ports of the first and second accelerators 104, 106 to the first and second turning magnets 108, 110. The first turning magnet 108 is connected to the second turning magnet 110 by vacuum electron beam guide 116 which is configured to guide a pulsed beam of accelerated electrons from the second turning magnet 110 to the first turning magnet 108. The second turning magnet 110 is adapted to turn the pulsed beam of accelerated electrons emitted by the second accelerator 106 in a direction toward the first turning magnet 108 when an energizing pulse is applied to the second turning magnet 110. The first turning magnet 108 is adapted to turn the pulsed beam of accelerated electrons emitted by the second accelerator 106 (and received from the second turning magnet 110) in a direction toward the conversion target 118 (described below) when an energizing pulse is applied to the first turning magnet 108.

The non-intrusive inspection system 100 also comprises a conversion target 118 and a collimator 120. The conversion target 118 is connected, via vacuum electron beam guide 122, to the first turning magnet 108. The vacuum electron beam guide 122 is adapted to direct a pulsed beam of accelerated electrons from the first turning magnet 108 to the conversion target 118. The conversion target 118 is operable to receive pulses of electrons of a pulsed beam of accelerated electrons from vacuum electron beam guide 122 and to convert the received pulses of electrons into a pulsed bremsstrahlung (also sometimes referred to herein as "x-ray") beam 124 that is emitted, or output, from the conversion target 118 and directed toward the collimator 120. Generally, the pulsed bremsstrahlung beam 124 includes different first and second energy spectra corresponding to the first and second energy levels of the respective pulses of electrons that are present in the pulsed beams of accelerated electrons emitted by the first and second accelerators 104, 106.

The collimator 120, generally, includes an elongate, narrow opening (e.g., a slot) through which a portion of the pulsed bremsstrahlung beam 124 passes to create a pulsed bremsstrahlung beam 126 having a beam shape suitable for cargo container inspection. Preferably, the pulsed bremsstrahlung beam 126 has a fan shape upon exiting the collimator 120. The collimator 120 is, typically, mounted to and/or integrated into a wall 128 separating an accelerator room 130 in which the first and second accelerators 104, 106, first and second turning magnets 108, 110, and conversion target 118 reside and an inspection room 132 through which cargo containers 102 are moved and exposed to the pulsed bremsstrahlung beam 126 exiting the collimator 120. During inspection, the cargo containers 102 are, generally, moved in a linear direction of travel that is perpendicular to the direction of the longitudinal axis 134 of the first accelerator 104. As a consequence, the pulsed bremsstrahlung beam 124 is directed predominantly at a first side of each cargo container 102 such that a substantial portion of it passes through the cargo container 102 (and the contents thereof) and through a second, opposing side of each cargo container 102.

The non-intrusive inspection system 100 additionally comprises a detector system 136 having a detector array 138 with a plurality of detectors 140 that are each operable to receive a portion of the pulsed bremsstrahlung beam 126 after it passes through a cargo container 102 and to produce an electrical signal representative thereof. The detector array 138, generally, has an "L" shape with a first portion 142 of the detector array 138 being oriented in a substantially vertical plane perpendicular to the direction of the longitudinal axis 134 of the first accelerator 104 and substantially parallel to and adjacent a side of a cargo container 102 as the cargo container 102 travels through the inspection room 132. The detector array 138 also has a second portion 144 that is oriented in a substantially horizontal plane perpendicular to the substantially vertical plane of the first portion 142 thereof such that the second portion 144 of the detector array 138 extends at least partially above a top of a cargo container 102 as the cargo container 102 travels through the inspection room 132. In order to enable the reception of portions of the pulsed bremsstrahlung beam 126 that may pass through the top, or roof, of a cargo container 102, some of the individual detectors 140 of the second portion 144 of the detector array 138 are oriented in a direction toward, or facing, the collimator 120 as opposed to being oriented in a downward direction perpendicular to the top of a cargo container 102 passing through the inspection room 132. It should be noted that because the non-intrusive inspection system 100 exposes a cargo container 102 to only one pulsed bremsstrahlung beam 126 that is, generally, directed in a direction substantially perpendicular to the first portion 144 of the detector array 138 (i.e., which includes the majority of the individual detectors 140 and, hence, provides the non-intrusive inspection system 100 with, essentially, detection and imaging capability in only plane), the non-intrusive inspection system 100 is, typically, categorized as a "single-plane inspection system".

Although not described in detail herein, the non-intrusive inspection system 100 further comprises various other components, including an imaging subsystem having data communication equipment and computer systems with appropriate software, that are configured to receive and transform electrical signals produced by the detector array 138 into images of the contents of a cargo container 102 for display to inspection system operators. The images produced by the imaging subsystem, generally, comprise two-dimensional, single plane views of the contents of a cargo container 102 taken from the perspective of a side thereof such that an image may extend between the container's ends and the container's top and bottom. However, because the non-intrusive inspection system 100 comprises a single-plane inspection system, the images do not include a view of the contents of a cargo container 102 taken from the perspective of a top or bottom thereof.

The non-intrusive inspection system 100 further comprises a material discrimination system that is connected to and receives electrical signals from the detector array 138 and that identifies, or discriminates, various materials present in the contents of a cargo container 102. Such material discrimination is possible because the non-intrusive inspection system 100 utilizes two pulsed beams of accelerated electrons that, respectively, include pulses of electrons having first and second energy levels and exposes a cargo container 102 to a pulsed bremsstrahlung beam 126 having first and second energy spectra (i.e., due to the creation of the pulsed bremsstrahlung beam 126 from pulses of electrons having first and second energy levels). The material discrimination subsystem is operable to receive data corresponding to the x-ray pulses that pass through the opposing sides of a cargo container 102 in the form of electrical signals received from the detector array 138. The material discrimination subsystem is further operable to analyze the received data and, using methods known to one of ordinary skill in the art, to identify and/or discriminate the materials present in the contents of a cargo container 102.

FIG. 2 displays a top plan, schematic sectional view of the non-intrusive inspection system 100 of FIG. 1 in accordance with the first exemplary embodiment of the present invention. As seen in FIG. 2, the first and second accelerators 104, 106 are positioned in a substantially side-by-side arrangement such that the directions of the pulsed beams of accelerated electrons emitted by the first and second accelerators 104, 106 are substantially parallel. Similarly, the first and second turning magnets 108, 110 are also positioned in a substantially side-by-side arrangement.

In operation, the first and second accelerators 104, 106 and first and second turning magnets 108, 110 of the non-intrusive inspection system 100 are appropriately controlled to produce a pulsed beam of accelerated electrons impinging on the conversion target 118 that alternately includes pulses of electrons from the first accelerator 104 and pulses of electrons from the second accelerator 106. The pulses of electrons from the first accelerator 104 have a first energy level and the pulses of electrons from the second accelerator 106 have a second energy level. Because the pulses of electrons in the beam impinging on the conversion target 118 alternate between first and second energy levels, the pulsed bremsstrahlung beam 124 emitted by the conversion target 118 includes different energy spectra corresponding to the first and second energy levels which enables discrimination of the materials present in the contents of a cargo container 102.

More specifically, at a first time, the first accelerator 104 is operated to generate a pulse of electrons having a first energy level that is directed to the first turning magnet 108 by vacuum electron beam guide 112. Concurrently, no energizing pulse is applied to the first turning magnet 108, thereby placing the first turning magnet 108 into a de-energized state and allowing the pulse of electrons from the first accelerator 104 to pass through the first turning magnet 108 and, in an unchanged direction, toward the conversion target 118 through vacuum electron beam guide 122. At a second time subsequent to the first time, the second accelerator 106 is operated to generate a pulse of electrons having a second energy level that is guided to the second turning magnet 110 by vacuum electron beam guide 114. Concurrently, energizing pulses are applied to the first and second turning magnets 108, 110, thereby placing the first and second turning magnets 108, 110 into energized states. When so energized, the second turning magnet 110 receives the pulse of electrons from the second accelerator 106 and turns, or directs, it in a new direction toward the first turning magnet 108 via vacuum electron beam guide 116. The first turning magnet 108, when so energized, receives the pulse of electrons from the second accelerator 106 and turns, or directs, it in a direction toward the conversion target 118 through vacuum electron beam guide 122.

Upon receiving the pulse of electrons having a first energy level produced by the first accelerator 104 at the first time, the conversion target 118 converts the received pulses of electrons into bremsstrahlung (or x-rays) having first energy spectra corresponding to the first energy level of the pulse of electrons from the first accelerator 104. The produced bremsstrahlung is then emitted from the conversion target 118 in a direction toward the collimator 120. At the second time, the conversion target 118 receives the pulse of electrons having a second energy level from the second accelerator 106 and converts the received pulse of electrons into bremsstrahlung (or x-rays) having second energy spectra corresponding to the second energy level of the pulse. The bremsstrahlung having second energy spectra is then emitted from the conversion target 118 in a direction toward the collimator 120.

Operation of the first and second accelerators 104, 106 and first and second turning magnets 108, 110 continues in such an alternating manner during operation of the non-intrusive inspection system 100 to produce, when integrated over time, the pulsed beam of accelerated electrons having pulses of electrons with alternating first and second energy levels that impinges on the conversion target 118. Similarly, operation of the conversion target 118 continues in such an alternating manner to produce and emit, when integrated over time, the pulsed bremsstrahlung (or x-ray) beam 124 having first and second spectra that is directed toward the collimator 120. As the pulsed bremsstrahlung beam 124 passes through the elongate, narrow opening of the collimator 120, the pulsed bremsstrahlung beam 124 is shaped to produce the pulsed bremsstrahlung beam 126 that exits the collimator 120 and impinges predominantly upon a side of a cargo container 102 being moved through the inspection room 132. The pulsed bremsstrahlung beam 126 passes through the opposing sides, or walls, of the cargo container 102 and objects present within the cargo container 102 such that different portions of the beam 126 impinge upon different detectors 140 of the detector array 138. The detectors 140, upon receiving respective portions of the pulsed bremsstrahlung beam 126, each produce an electrical signal representative of the portion of the pulsed bremsstrahlung beam 126 received thereby. The detector system 136 communicates the produced electrical signals, or an equivalent thereof, to the imaging and material discrimination subsystems for the generation of single plane, two-dimensional images representative of the contents of (or, objects present within) the cargo container 102 and for the discrimination and identification of materials present in such objects.

FIG. 3 displays a timing diagram illustrating the relative timing of the alternating electron beam current pulses of the pulsed beam of accelerated electrons impinging on the conversion target 118, the alternating pulses of the pulsed bremsstrahlung beam 126, and the energizing signals applied to the first and second turning magnets 108, 110, in accordance with the first exemplary embodiment of the present invention. As illustrated in FIG. 3, at a first time denoted by the number "1" on the horizontal time axis of the timing diagram, no energizing signal (i.e., current) is applied to the first turning magnet 108 as indicated by the magnet current, $I_{kick}$, having a value of zero. At the first time, the first accelerator 104 emits an electron beam current pulse and the second accelerator 106 emits no electron beam current pulse. Therefore, at the first time, the pulsed beam of accelerated electrons impinging on the conversion target 118 comprises an electron beam current pulse from the first accelerator 104 (i.e., denoted by a positive beam current, $I_{hor-max}$) and no electron beam current pulse from the second accelerator 106 (i.e., denoted by a zero beam current, $I_{hor-min}$). Consequently, at the first time, the pulsed bremsstrahlung beam 126 comprises a bremsstrahlung pulse having a first energy spectra (i.e., denoted by a low level pulse on the $B_{hor}$ axis).

At a second time denoted by the number "2" on the horizontal time axis of the timing diagram, an energizing signal (i.e., current) is applied to the first and second turning magnets 108, 110 as indicated by the magnet current, $I_{kick}$, having a non-zero value. At the second time, the pulsed beam of accelerated electrons impinging on the conversion target 118 comprises an electron beam current pulse from the second accelerator 106 (i.e., denoted by a positive beam current, $I_{hor-min}$) and no'electron beam current pulse from the first accelerator 104 (i.e., denoted by a zero beam current, $I_{hor-max}$). Consequently, at the second time, the pulsed bremsstrahlung beam 126 comprises a bremsstrahlung pulse having a second energy spectra (i.e., denoted by a high level pulse on the $B_{hor}$ axis). As additionally illustrated in FIG. 3, the timing of pulses at the first and second times (i.e., "1" and "2") is repeated at respectively successive times with the beam currents and energy spectra corresponding to the first time being repeated at successive odd numbered times and the beam currents and energy spectra corresponding to the second time being repeated at successive even numbered times.

Figure 4:
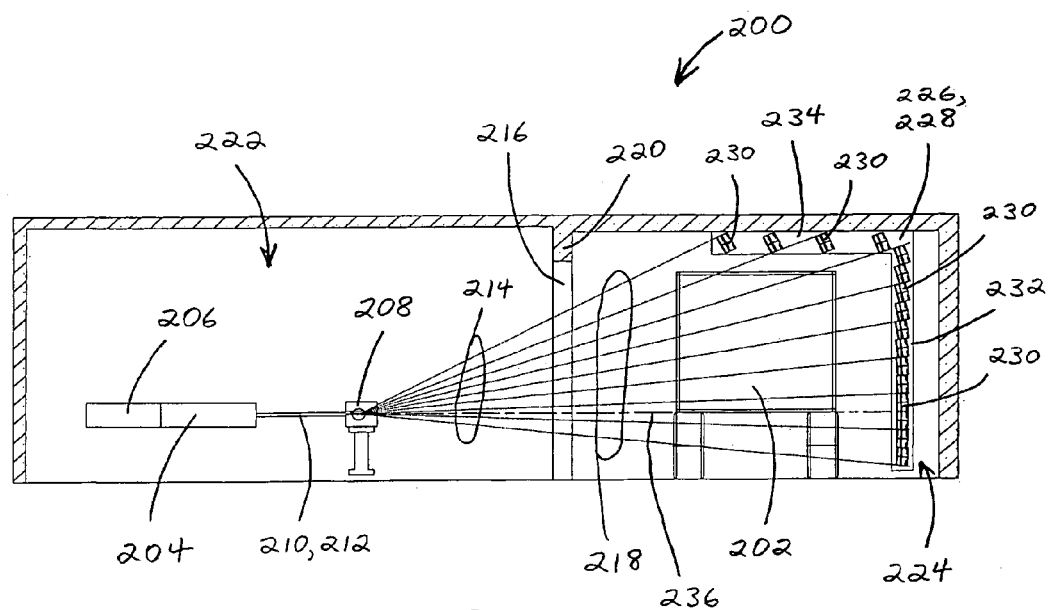
FIG. 4 displays a side elevation, schematic sectional view of a non-intrusive inspection system for inspecting the contents of a cargo container in accordance with a second exemplary embodiment of the present invention.

FIG. 4 displays a side elevation, schematic sectional view of a non-intrusive inspection system 200 for inspecting the contents of a cargo container 202 in accordance with a second exemplary embodiment of the present invention. The non-intrusive inspection system 200 comprises first and second accelerators 204, 206 and a conversion target 208. The first accelerator 204 comprises a pulse-type, electron accelerator that is operable to produce, or emit, a pulsed beam of accelerated electrons in a first direction including a plurality of electron pulses having a first energy level. The second accelerator 206 comprises a pulse-type, electron accelerator that is operable to produce, or emit, a pulsed beam of accelerated electrons in a second direction including a plurality of electron pulses having a second energy level. Generally, the first and second energy levels are different, as are the first and second directions. The output ports of the first and second accelerators 204, 206 are connected to the conversion target 208 by respective vacuum electron beam guides 210, 212 that are adapted to guide respective pulsed beams of accelerated electrons from the output ports of the first and second accelerators 204, 206 in different directions to the conversion target 208.

The conversion target 208 is operable to receive pulses of electrons of the pulsed beams of accelerated electrons emitted by the first and second accelerators 204, 206 through vacuum electron beam guides 210, 212 and to convert the received pulses of electrons into a pulsed bremsstrahlung (or x-ray) beam 214 that is emitted, or output, from the conversion target 208. Generally, the pulsed bremsstrahlung beam 214 includes first and second energy spectra corresponding to the first and second energy levels of the respective pulses of electrons that are present in the pulsed beams of accelerated electrons emitted by the first and second accelerators 204, 206.

The non-intrusive inspection system 200 also comprises a collimator 216 at which the pulsed bremsstrahlung beam 214 emitted by the conversion target 208 is directed. The collimator 216, generally, includes an elongate, narrow opening (e.g., a slot) through which a portion of the pulsed bremsstrahlung beam 214 passes to create a pulsed bremsstrahlung beam 218 having a beam shape suitable for cargo container inspection. Preferably, the pulsed bremsstrahlung beam 218 has a fan shape upon exiting the collimator 216. The collimator 216 is, typically, mounted to and/or integrated into a wall 220 separating an accelerator room 222 in which the first and second accelerators 204, 206 and conversion target 208 reside and an inspection room 224 through which cargo containers 202 are moved and exposed to the pulsed bremsstrahlung beam 218 exiting the collimator 216. During inspection the cargo containers 202 are, generally, moved in a linear direction of travel that is perpendicular to the direction of the longitudinal axis 236 of the first accelerator 204. As a consequence, the pulsed bremsstrahlung beam 214 is directed predominantly at a first side of each cargo container 202 such that a substantial portion of it passes through the cargo container 202 (and the contents thereof and through a second, opposing side of each cargo container 202.

The non-intrusive inspection system 200 additionally comprises a detector system 226 having a detector array 228 with a plurality of detectors 230 that are each operable to receive a portion of the pulsed bremsstrahlung beam 218 after it passes through a cargo container 202 and to produce an electrical signal representative thereof. The detector array 228, generally, has an "L" shape with a first portion 232 of the detector array 228 being oriented in a substantially vertical plane perpendicular to the direction of the longitudinal axis 236 of the first accelerator 204 and substantially parallel to and adjacent a side of a cargo container 202 as the cargo container 202 travels through the inspection room 224. The detector array 228 also has a second portion 234 that is oriented in a substantially horizontal plane perpendicular to the substantially vertical plane of the first portion 232 thereof such that the second portion 234 of the detector array 228 extends at least partially above a top, or roof, of a cargo container 202 as the cargo container 202 travels through the inspection room 224. In order to enable the reception of portions of the pulsed bremsstrahlung beam 218 that may pass through the top, or roof, of a cargo container 202, some of the individual detectors 230 of the second portion 234 of the detector array 228 are oriented in a direction toward, or facing, the collimator 216 as opposed to being oriented in a downward direction perpendicular to the top of a cargo container 202 passing through the inspection room 224. It should be noted that because the non-intrusive inspection system 200 exposes a cargo container 202 to only one pulsed bremsstrahlung beam 218 that is, generally, directed in a direction substantially perpendicular to the first portion 232 of the detector array 228 (i.e., which includes the majority of the individual detectors 230 and, hence, provides the non-intrusive inspection system 200 with detection and imaging capability in only plane), the non-intrusive inspection system 200 is, typically, categorized as a "single-plane inspection system".

Although not described in detail herein, the non-intrusive inspection system 200 further comprises various other components, including an imaging subsystem having data communication equipment and computer systems with appropriate software, that are configured to receive and transform electrical signals produced by the detector array 228 into images of the contents of a cargo container 202 for display to inspection system operators. The images produced by the imaging subsystem, generally, comprise two-dimensional views of the contents of a cargo container 202 taken from the perspective of a side thereof such that an image may extend between the container's ends and the container's top and bottom. However, because the non-intrusive inspection system 200 comprises a single-plane inspection system, the images do not include a view of the contents of a cargo container 202 taken from the perspective of a top or bottom thereof.

The non-intrusive inspection system 200 further comprises a material discrimination subsystem that is connected to and receives electrical signals from the detector array 228 and that identifies, or discriminates, various materials present in the contents of a cargo container 202. Such material discrimination is possible because the non-intrusive inspection system 200 utilizes two pulsed beams of accelerated electrons that, respectively, include pulses of electrons having first and second energy levels and exposes a cargo container 202 to a pulsed bremsstrahlung beam 218 having first and second energy spectra (i.e., due to the creation of the pulsed bremsstrahlung beam 218 from pulses of electrons having first and second energy levels). The material discrimination subsystem is operable to receive data corresponding to the x-ray pulses that pass through the opposing sides of a cargo container 202 in the form of electrical signals received from the detector array 228. The material discrimination subsystem is further operable to analyze the received data and, using methods known to one of ordinary skill in the art, to identify and/or discriminate the materials present in the contents of a cargo container 202.

FIG. 5 displays a top plan, schematic sectional view of the non-intrusive inspection system 200 of FIG. 4 in accordance with the second exemplary embodiment of the present invention. As seen in FIG. 5, the first and second accelerators 204, 206 are positioned in an arrangement such that the longitudinal axes of the first and second accelerators 204, 206 and the vacuum electron beam guides 210, 212 (and, hence, the directions of the pulsed beams of accelerated electrons emitted by the first and second accelerators 204, 206) define an angle, $\alpha$, therebetween. Generally, angle, $\alpha$, comprises an acute angle. Further, angle, $\alpha$, may have an angular measure between zero and forty-five degrees.

In operation, the first and second accelerators 204, 206 of the non-intrusive inspection system 200 are appropriately controlled to produce respective first and second pulsed beams of accelerated electrons alternately impinging on the conversion target 208 from respective first and second directions. Thus, the conversion target 208 alternately receives pulses of electrons from the first accelerator 204 and pulses of electrons from the second accelerator 206. The pulses of electrons from the first accelerator 204 have a first energy level and the pulses of electrons from the second accelerator 206 have a second energy level. Because the pulses of electrons in the beams impinging on the conversion target 208 alternate between different first and second energy levels, the pulsed bremsstrahlung beam 214 emitted by the conversion target 208 includes first and second spectra corresponding to the first and second energy levels which enables discrimination of the materials present in the contents of a cargo container 202.

More specifically, at a first time, the first accelerator 204 is operated to generate a pulse of electrons having a first energy level that is directed in a first direction toward the conversion target 208 by vacuum electron beam guide 210. At a second time subsequent to the first time, the second accelerator 206 is operated to generate a pulse of electrons having a second energy level that is guided in a second direction toward the conversion target 208 by vacuum electron beam guide 212 at an angle, $\alpha$, relative to the pulse of electrons generated by the first accelerator 204.

Upon receiving the pulse of electrons having a first energy level produced by the first accelerator 204 at the first time, the conversion target 208 converts the received pulses of electrons into bremsstrahlung (or x-rays) having first energy spectra corresponding to the first energy level of the pulse of electrons from the first accelerator 204. The produced bremsstrahlung is then emitted from the conversion target 208 in a direction toward the collimator 216. At the second time, the conversion target 208 receives the pulse of electrons having a second energy level from the second accelerator 206 and converts the received pulse of electrons into bremsstrahlung (or x-rays) having second energy spectra corresponding to the second energy level of the pulse. The bremsstrahlung having second energy spectra is then emitted from the conversion target 208 in a direction toward the collimator 216.

Operation of the first and second accelerators 204, 206 continues in such an alternating manner during operation of the non-intrusive inspection system 200 to produce, when integrated over time, the respective pulsed beams of accelerated electrons that impinge on the conversion target 208. Similarly, operation of the conversion target 208 continues in such an alternating manner to produce, when integrated over time, the pulsed bremsstrahlung (or x-ray) beam 214 having first and second energy spectra that is directed toward the collimator 216. As the pulsed bremsstrahlung beam 214 passes through the elongate, narrow opening of the collimator 216, the pulsed bremsstrahlung beam 214 is shaped to produce the pulsed bremsstrahlung beam 218 that exits the collimator 216 and impinges predominantly upon a side of a cargo container 202 being moved through the inspection room 224. The pulsed bremsstrahlung beam 218 passes through the opposing sides and walls of the cargo container 202 and objects present within the cargo container 202 such that different portions of the beam 218 impinge-upon different detectors 230 of the detector array 228. The detectors 230, upon receiving respective portions of the pulsed bremsstrahlung beam 218, each produce an electrical signal representative of the portion of the pulsed bremsstrahlung beam 218 received thereby. The detector system 226 communicates the produced electrical signals, or an equivalent thereof, to the imaging and material discrimination subsystems for the generation of single plane, two-dimensional images representative of the contents of (or, objects present within) the cargo container 202 and for the discrimination and identification of materials present in such objects.

FIG. 6 displays a timing diagram illustrating the relative timing of the alternating electron beam current pulses of the pulsed beams of accelerated electrons impinging on the conversion target 208 and the alternating pulses of the pulsed bremsstrahlung beam 218, in accordance with the second exemplary embodiment of the present invention. As illustrated in FIG. 6, at a first time denoted by the number "1" on the horizontal time axis of the timing diagram, the first accelerator 204 emits an electron beam current pulse and the second accelerator 206 emits no electron beam current pulse. Therefore, at the first time, the pulsed beam of accelerated electrons impinging on the conversion target 208 comprises an electron beam current pulse from the first accelerator 204 (i.e., denoted by a positive beam current, $I_{hor-max}$) and no electron beam current pulse from the second accelerator 206 (i.e., denoted by a zero beam current, $I_{hor-min}$). Consequently, at the first time, the pulsed bremsstrahlung beam 218 comprises a bremsstrahlung (or x-ray) pulse having a first energy spectra (i.e., denoted by a low level pulse on the $B_{hor}$ axis).

At a second time denoted by the number "2" on the horizontal time axis of the timing diagram, the first accelerator 204 emits no electron beam current pulse and the second accelerator 206 emits an electron beam current pulse. Therefore, the pulsed beam of accelerated electrons impinging on the conversion target 208 comprises an electron beam current pulse from the second accelerator 206 (i.e., denoted by a positive beam current, $I_{hor-min}$) and no electron beam current pulse from the first accelerator 204 (i.e., denoted by a zero beam current, $I_{hor-max}$) Consequently, at the second time, the pulsed bremsstrahlung beam 218 comprises a bremsstrahlung (or x-ray) pulse having a second energy spectra (i.e., denoted by a high level pulse on the $B_{hor}$ axis). As additionally illustrated in FIG. 6, the timing of pulses at the first and second times (i.e., "1" and "2") is repeated at respectively successive times with the beam currents and energy spectra corresponding to the first time being repeated at successive odd numbered times and the beam currents and energy spectra corresponding to the second time being repeated at successive even numbered times.

FIG. 7 displays a side elevation, schematic sectional view of a non-intrusive inspection system 300 for inspecting the contents of a cargo container 302 in accordance with a third exemplary embodiment of the present invention. The non-intrusive inspection system 300 comprises an accelerator 304, a first turning magnet 306 (also sometimes referred to as a "first kicker magnet 306), and a first conversion target 308. Generally, the accelerator 304 comprises a pulse-type, electron accelerator that is operable to produce, or emit, a pulsed beam of accelerated electrons including a plurality of electron pulses having a particular, single energy level. The output port of the accelerator 304 and the first turning magnet 306 are connected by a first vacuum electron beam guide 310 which is adapted to guide the pulsed beam of accelerated electrons in a first direction from the output port of the accelerator 304 to the first turning magnet 310. The first turning magnet 306 is adapted to turn the pulsed beam of accelerated electrons emitted by the accelerator 304 (and received via first vacuum electron beam guide 310) in a new direction when an energizing pulse of electrical current is applied thereto and to allow the pulsed beam of accelerated electrons to pass therethrough without turning when no energizing pulse of current is applied thereto. The first turning magnet 310 and the first conversion target 308 are connected by a second vacuum electron beam guide 312 that is configured to direct the pulsed beam of accelerated electrons from the first turning magnet 310 to the first conversion target 308.

The first conversion target 308 is operable to receive pulses of electrons of the pulsed beam of accelerated electrons from the second vacuum electron beam guide 312 and to emit a corresponding first pulsed bremsstrahlung (or x-ray) beam 314 that is output from the conversion target 308 and directed toward a first collimator 316. Generally, the first pulsed bremsstrahlung beam 314 includes energy spectra corresponding to the energy level of the pulses of electrons that are present in the pulsed beam of accelerated electrons emitted by the accelerator 304.

The first collimator 316, typically, includes an elongate, narrow opening (e.g., a slot) through which a portion of the first pulsed bremsstrahlung beam 314 passes to produce a second pulsed bremsstrahlung beam 318 having a beam shape suitable for cargo container inspection. Preferably, the second pulsed bremsstrahlung beam 318 has a fan shape upon exiting the first collimator 316. The first-collimator 316 is, generally, mounted to and/or integrated into a wall 320 separating an accelerator room 322 in which the accelerator 304, first turning magnet 306, and first conversion target 308 reside and an inspection room 324 through which cargo containers 302 are moved and exposed to the second pulsed bremsstrahlung beam 318 exiting the first collimator 316. During inspection, the cargo containers 302 are, generally, moved in a linear direction of travel that is perpendicular to the direction of the longitudinal axis 325 of the accelerator 304 such that the second pulsed bremsstrahlung beam 318 is directed at and impinges on a side of each cargo container 302 while moving through the inspection room 324.

The non-intrusive inspection system 300 also comprises a second turning magnet 326, a third turning magnet 328, and a second conversion target 330. The second turning magnet 326 (also sometimes referred to as a "second kicker magnet 326") is, typically, located in a first auxiliary room 332 substantially beneath the accelerator room 322 at a position elevationally below the first turning magnet 306. First and second triplets 334, 336 (e.g., sets of focusing lenses) are interposed between the first and second turning magnets 306, 326 to refocus the pulsed beam of accelerated electrons emitted by the accelerator 304. The first triplet 334 is connected to the first turning magnet 306 by a third vacuum electron beam guide 338 which is adapted to guide the pulsed beam of accelerated electrons from the first turning magnet 310 to the input of the first triplet 334. A fourth vacuum electron beam guide 340 is connected to the output of the first triplet 334 and to the input of the second triplet 336, and is configured to direct the pulsed beam of accelerated electrons from the first triplet 334 to the second triplet 336. The output of the second triplet 336 is connected to the input of the second turning magnet 326 by a fifth vacuum electron beam guide 342 that is adapted to guide the pulsed beam of accelerated electrons from the second triplet 336 to the second turning magnet 326. The second turning magnet 326 is adapted to turn the pulsed beam of accelerated electrons emitted by the accelerator 304 (and received via fifth vacuum electron beam guide 342) in a new direction toward the third turning magnet 328 when an energizing pulse of electrical current is applied thereto (i.e., which may occur continuously or only when a similar energizing pulse of electrical current is applied to the first turning magnet 306).

The third turning magnet 328 (also sometimes referred to as a "third kicker magnet 328") is, typically, located in a second auxiliary room 344 substantially beneath the inspection room 324 at a position having an elevation substantially equal to the elevation of the position of the second turning magnet 326. Third and fourth triplets 346, 348 (e.g., sets of focusing lenses) are interposed between the second and third turning magnets 326, 328 to refocus the pulsed beam of accelerated electrons emitted by the accelerator 304. The third triplet 346 is connected to the second turning magnet 326 by a sixth vacuum electron beam guide 350 which is adapted to guide the pulsed beam of accelerated electrons from the second turning magnet 326 to the input of the third triplet 346. A seventh vacuum electron beam guide 352 is connected to the output of the third triplet 346 and to the input of the fourth triplet 348, and is configured to direct the pulsed beam of accelerated electrons from the third triplet 346 to the fourth triplet 348. The output of the fourth triplet 348 is connected to the input of the third turning magnet 328 by an eighth vacuum electron beam guide 354 that is adapted to guide the pulsed beam of accelerated electrons from the fourth triplet 348 to the third turning magnet 328. The third turning magnet 328 is adapted to turn the pulsed beam of accelerated electrons emitted by the accelerator 304 (and received via eighth vacuum electron beam guide 354) in a new direction toward the second conversion target 330 when an energizing pulse of electrical current is applied thereto (i.e., which may occur continuously or only when a similar energizing pulse of electrical current is applied to the first and second turning magnets 306, 328).

The second conversion target 330 is connected to the third turning magnet 328 by a ninth vacuum electron beam guide 356 extending therebetween that is adapted to guide pulses of electrons of the pulsed beam of accelerated electrons in a direction toward the second conversion target 330. The second conversion target 330 is operable to receive pulses of electrons of the pulsed beam of accelerated electrons from the ninth vacuum electron beam guide 356 and to convert the received pulses of electrons into a third pulsed bremsstrahlung (i.e., x-ray) beam 358 that is emitted, or output, from the second conversion target 330 in a direction toward a second collimator 360. Generally, the third pulsed bremsstrahlung beam 358 includes energy spectra corresponding to the single energy level of the pulses of electrons that are present in the pulsed beam of accelerated electrons emitted by the accelerator 304.

The second collimator 360, typically, includes an elongate, narrow opening (e.g., a slot) through which a portion of the third pulsed bremsstrahlung beam 358 passes to produce a fourth pulsed bremsstrahlung beam 362 having a beam shape suitable for cargo container inspection. Preferably, the fourth pulsed bremsstrahlung beam 362 has a fan shape upon exiting the second collimator 360. The second collimator 360 is, generally, mounted to and/or integrated into a wall 364 separating the second auxiliary room 344 in which the third turning magnet 328 and second conversion target 330 reside and the inspection room 324 through which cargo containers 302 are moved and exposed to the fourth pulsed bremsstrahlung beam 362 exiting the second collimator 360. During inspection, the cargo containers 302 are, generally, moved by a conveyor 365 in a linear direction of travel that is perpendicular to a vertical axis 366 extending through the second conversion target 330 such that the fourth pulsed bremsstrahlung beam 362 is directed, generally, at and impinges on the bottom of each cargo container 302 during movement thereof through the inspection room 324.

The non-intrusive inspection system 300 additionally comprises a detector system 368 having a detector array 370 with a plurality of detectors 372 that are each operable to receive a portion of the second and fourth pulsed bremsstrahlung beams 318, 362 after they pass through a cargo container 302 and produce electrical signals representative thereof. The detector array 370, generally, has an "L" shape with a first portion 374 thereof being oriented in a substantially vertical plane perpendicular to the longitudinal axis 325 of the accelerator 304 and substantially parallel to and adjacent a side of a cargo container 302 as the cargo container 302 travels through the inspection room 324. The detector array 370 also has a second portion 376 that is oriented in a substantially horizontal plane perpendicular to the substantially vertical plane of the first portion 374 thereof and perpendicular to the vertical axis 366 extending through the second conversion target 330 such that the second portion 376 of the detector array 370 extends at least partially above a top, or roof, of a cargo container 302 as the cargo container 302 travels through the inspection room 324.

In order to enable the reception of portions of the second pulsed bremsstrahlung beam 318 that may pass through the top, or roof, of a cargo container 302, some of the individual detectors 372 of the second portion 376 of the detector array 370 are slightly turned in a direction somewhat toward, or facing, the first collimator 316 as opposed to being oriented entirely in a downward direction perpendicular to the horizontal plane of the second portion 376 of the detector array 370. Similarly, in order to enable the reception of portions of the fourth pulsed bremsstrahlung beam 362 that may pass through a side of a cargo container 302, some of the individual detectors 372 of the first portion 374 of the detector array 370 are slightly turned in a direction somewhat toward, or facing, the second collimator 360 as opposed to being oriented entirely in a direction perpendicular to the vertical plane of the first portion 374 of the detector array 370. It should be noted that because the non-intrusive inspection system 300 exposes a cargo container 302 to two pulsed bremsstrahlung beams 318, 362 and has a detector array 370 that is fully populated with detectors 372 for detection and imaging capability in two planes (i.e., the vertical plane of the first portion 374 of the detector array 370 and the horizontal plane of the second portion 376 of the detector array 370), the non-intrusive inspection system 300 of the third exemplary embodiment is, typically, categorized as a "dual-plane inspection system".

Although not described in detail herein, the non-intrusive inspection system 300 further comprises various other components, including an imaging subsystem having data communication equipment and computer systems with appropriate software, that are configured to receive and transform electrical signals produced by the detector array 370 into images of the contents of a cargo container 302 for display to inspection system operators. The images produced by the imaging subsystem, generally, comprise two-dimensional views of the contents of a cargo container 302 taken from the perspective of a side thereof such that a first image may extend between the container's ends and the container's top and bottom, and taken from the perspective of the bottom thereof such that a second image may extend between the container's ends and the container's sides. It should be noted, however, that because the non-intrusive inspection system 300 utilizes a single accelerator 304 that produces a pulsed beam of accelerated electrons having only a single energy level and exposes a cargo container 302 to pulsed bremsstrahlung beams 318, 362 having the same energy spectra (i.e., due to the creation of the pulsed bremsstrahlung beams 318, 362 from the pulsed beam of electrons having a single energy level), the non-intrusive inspection system 300 does not enable the discrimination and identification of materials present in the contents of (or, objects present within) a cargo container 302 as do other the non-intrusive inspection systems of certain other embodiments described herein.

FIG. 8 displays a top plan, schematic sectional view of the non-intrusive inspection system 300 of FIG. 7 in accordance with the third exemplary embodiment of the present invention. As seen in FIG. 8, the accelerator 304 is positioned such that the accelerator's longitudinal axis 325 is perpendicular to the first portion 374 of the detector array 370 and perpendicular to the direction of travel of the cargo container 302 through the inspection room 324. Notably, the second turning magnet 326 is located directly beneath the first turning magnet 306.

In operation, the accelerator 304 and the first, second and third turning magnets 306, 326, 328 of the non-intrusive inspection system 300 are appropriately controlled to produce a pulsed beam of accelerated electrons with odd numbered pulses of electrons thereof being directed in a direction toward the first conversion target 308 and even numbered pulses of electrons thereof being directed toward the second conversion target 330. The pulses of electrons produced by the accelerator 304 all have a single energy level and, as a consequence, the first and second pulsed bremsstrahlung beams 318, 362 generated by the first and second conversion targets 308, 330 each include the same energy spectra. Because two pulsed bremsstrahlung beams 318, 362 are employed with a detector array 370 capable of detecting portions of the pulsed bremsstrahlung beams 318, 362, in horizontal and vertical planes, that pass respectively through opposing sides and the top and bottom of a cargo container 302, the non-intrusive inspection system 300 produces two-dimensional views of the cargo container 302 from different directions that, essentially, allow three-dimensional viewing of the contents of the cargo container 302. However, because the two pulsed bremsstrahlung beams 318, 362 each have only one energy spectra corresponding to the single energy level of the pulses of electrons produced by the accelerator 304, the non-intrusive inspection system 300 cannot distinguish between or identify materials present in the contents of, or objects in, a cargo container 302.

More specifically, at a first time, the accelerator 304 is operated to generate a first pulse of electrons having a single energy level that is directed to the first turning magnet 306 in a first direction by the first vacuum electron beam guide 310. At the first time, no energizing signal pulse (i.e., electrical current) is concurrently applied to the first turning magnet 306, thereby placing the first turning magnet 306 into a de-energized state and allowing the first pulse of electrons from the accelerator 304 to pass through the first turning magnet 306 absent a change in direction and on toward the conversion target 308 through the second vacuum electron beam guide 312. In response to receiving the first pulse of electrons, the conversion target 308 converts the first pulse of electrons into a pulse of bremsstrahlung (i.e., a pulse of first bremsstrahlung beam 314) having a single energy spectra corresponding to the single energy level of the first pulse of electrons from the first accelerator 304. The produced pulse of bremsstrahlung is emitted from the conversion target 308 in a direction toward the first collimator 316 which shapes the pulse of bremsstrahlung to produce a shaped pulse of bremsstrahlung (i.e., a pulse of second bremsstrahlung beam 316) which impinges upon a side of a cargo container 302 being moved through the inspection room 324.

At a second time, the accelerator 304 is operated to generate a second pulse of electrons having a single energy level that is directed in a first direction to the first turning magnet 306 by the first vacuum electron beam guide 310. At the second time, an energizing signal pulse (i.e., electrical current) is concurrently applied to the first turning magnet 306 and to the second and third turning magnets 326, 328 (or, alternatively, energizing signal pulses (i.e., electrical current) may be continuously applied to the second and third turning magnets 326, 328), thereby placing the first turning magnet 306 into an energized state and allowing the second pulse of electrons from the accelerator 304 to be turned by the first turning magnet 306 into a new direction toward the second turning magnet 326. After being turned by the first turning magnet 306, the second pulse of electrons travels through the first and second triplets 334, 336 and the third, fourth and fifth vacuum electron beam guides 338, 340, 342 to the second turning magnet 326. While traveling through the first and second triplets 334, 336, the second pulse of electrons is refocused to minimize dispersion of the electrons thereof.

Upon arriving at and passing through the energized second turning magnet 326, the second pulse of electrons is turned by the second turning magnet 326 into a direction toward the third turning magnet 328. The second pulse of electrons then travels through the third and fourth triplets 346, 348 and the sixth, seventh, and eighth vacuum electron beam guides 350, 352, 354 to the third turning magnet 328. While traveling through the third and fourth triplets 346, 348, the second pulse of electrons is once again re-focused to minimize dispersion of the electrons thereof.

After reaching the third turning magnet 328, the second pulse of electrons is turned by the third turning magnet 328 into a direction toward the second conversion target 330 and the bottom of a cargo container 302 passing through the inspection room 324. The second pulse of electrons then travels through the ninth vacuum electron beam guide 356 to the second conversion target 330. Upon receiving the second pulse of electrons, the second conversion target 330 converts the received second pulse of electrons into bremsstrahlung (i.e., a pulse of the third pulsed bremsstrahlung beam 358) having an energy spectra corresponding to the energy level of the pulses of electrons emitted from the accelerator 304 (and, hence, to the energy spectra of the first pulsed bremsstrahlung beam 314). The produced bremsstrahlung is then emitted from the second conversion target 330 in a direction toward the second collimator 360 which shapes the pulse of bremsstrahlung (or x-ray) to produce a shaped pulse of bremsstrahlung (i.e., a pulse of second pulsed bremsstrahlung beam 362) which impinges upon the bottom of a cargo container 302 being moved through the inspection room 324.

Operation of the accelerator 304 and the first, second and third turning magnets 306, 326, 328 continues in an alternating manner during operation of the non-intrusive inspection system 300 to direct odd numbered pulses of electrons produced by the accelerator 304 toward the first conversion target 308 and even numbered pulses of electrons produced by the accelerator 304 toward the second conversion target 330. The second and fourth pulsed bremsstrahlung (or x-ray) beams 318, 362 produced therefrom, as a consequence, comprise pulses of bremsstrahlung that impinge, respectively, upon a side and bottom of a cargo container 304 at alternating times, thereby causing the detectors 372 of the detector array 374 to alternately produce electrical signals representative of the portions of the pulses of bremsstrahlung that pass through the contents of a cargo container 302 from a side or bottom thereof and strike the detectors 372. The detector system 370 communicates the produced electrical signals, or an equivalent thereof, to the imaging subsystem for the generation of respective two-dimensional images representative of the contents of (or, objects present within) the cargo container 302 when viewed from a side and bottom thereof.

Figure 9:
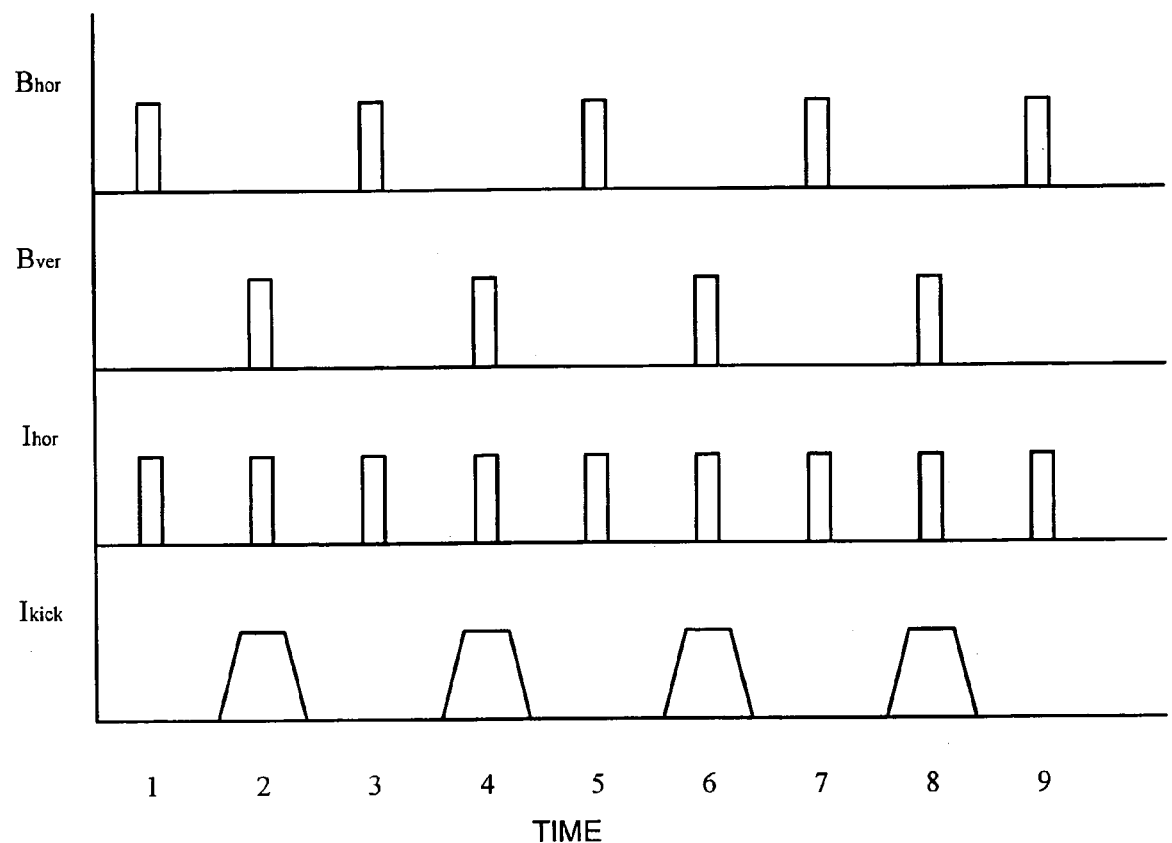
FIG. 9 displays a timing diagram illustrating the timing of various pulses during operation of the non-intrusive inspection system of FIG. 7 in accordance with the third exemplary embodiment of the present invention.

FIG. 9 displays a timing diagram illustrating the relative timing of the electron beam current pulses of the pulsed beam of accelerated electrons alternatingly impinging on the conversion targets 308, 330, the alternating bremsstrahlung pulses of the second and fourth pulsed bremsstrahlung beams 318, 362, and the energizing signals applied to the first, second and third turning magnets 306, 326, 328, in accordance with the third exemplary embodiment of the present invention. As illustrated in FIG. 9, at a first time denoted by the number "1" on the horizontal time axis of the timing diagram, no energizing signal (i.e., electrical current) is applied to the first, second and third turning magnets 306, 326, 328 as indicated by the magnet current, $I_{kick}$, having a zero value. At, the first time and by virtue of no energizing signal being applied to the first, second and third turning magnets 306, 326, 328, the accelerator 304 emits an electron beam current pulse that passes through the first turning magnet 306 without being turned. Therefore, at the first time, the electron beam current pulse emitted from the accelerator 304 impinges on the first conversion target 308, causing the generation of a pulse of bremsstrahlung of the first and second pulsed bremsstrahlung beams 314, 318 having an energy spectra (i.e., denoted by a pulse on the $B_{hor}$ axis) corresponding to the energy level of the electron beam current pulse.

At a second time denoted by the number "2" on the horizontal time axis of the timing diagram, an energizing signal (i.e., current) is applied to the first, second and third turning magnets 306, 326, 328 as indicated by the magnet current, $I_{kick}$, having a non-zero value. At the second time and by virtue of an energizing signal being applied to the first, second and third turning magnets 306, 326, 328, the accelerator 304 emits an electron beam current pulse that passes through the first turning magnet 306 and is turned in a new direction toward the second turning magnet 326. Therefore, at the second time, the electron beam current pulse emitted from the accelerator 304 impinges on the second conversion target 330, causing the generation of a pulse of bremsstrahlung of the third and fourth pulsed bremsstrahlung beams 358, 362 having an energy spectra (i.e., denoted by a pulse on the $B_{ver}$ axis) corresponding to the energy level of the electron beam current pulse. Notably, as illustrated in FIG. 9, the magnitude of each of the pulses of bremsstrahlung of the first, second, third and fourth bremsstrahlung beams 314, 316, 358, 362 is the same. As additionally illustrated in FIG. 9, the timing of pulses at the first and second times (i.e., "1" and "2") is repeated at respectively successive times with the beam currents and energy spectra corresponding to the first time being repeated at successive odd numbered times and the beam currents and energy spectra corresponding to the second time being repeated at successive even numbered times.

Figure 10:
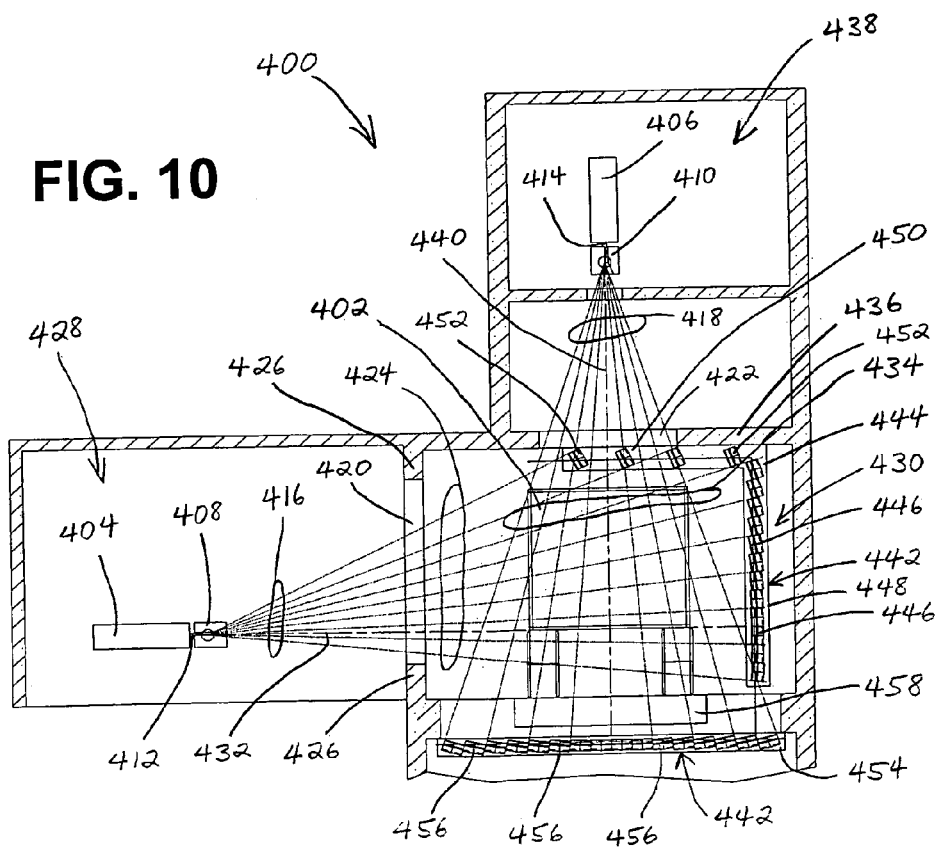
FIG. 10 displays a side elevation, schematic sectional view of a non-intrusive inspection system for inspecting the contents of a cargo container in accordance with a fourth exemplary embodiment of the present invention.

FIG. 10 displays a side elevation, schematic sectional view of a non-intrusive inspection system 400 for inspecting the contents of a cargo container 402 in accordance with a fourth exemplary embodiment of the present invention. The non-intrusive inspection system 400 comprises first and second accelerators 404, 406 and first and second conversion targets 408, 410. The first accelerator 404 comprises a pulse-type, electron accelerator that is operable to produce, or emit, a pulsed beam of accelerated electrons including pluralities of electron pulses having different first and second energy levels. The second accelerator 406 comprises a pulse-type, electron accelerator that is operable to produce, or emit, a pulsed beam of accelerated electrons including pluralities of electron pulses having different first and second energy levels. The output ports of the first and second accelerators 404, 406 are connected to respective first and second conversion targets 408, 410 by respective first and second vacuum electron beam guides 412, 414 that are adapted to guide the respective pulsed beams of accelerated electrons from the output ports of the first and second accelerators 404, 406 to the respective first and second conversion targets 408, 410.

The first and second conversion targets 408, 410 are operable to receive pulses of electrons of the pulsed beams of accelerated electrons respectively emitted by the first and second accelerators 404, 406 through first and second vacuum electron beam guides 412, 414 and to convert the received pulses of electrons into respective first and second pulsed bremsstrahlung (or x-ray) beams 416, 418 that are emitted, or output, from the first and second conversion targets 408, 410. Generally, the first and second pulsed bremsstrahlung beams 416, 418 include both first and second energy spectra corresponding to the first and second energy levels of the respective pulses of electrons that are present in the pulsed beams of accelerated electrons emitted by the first and second accelerators 404, 406.

The non-intrusive inspection system 400 also comprises first and second collimators 420, 422 at which the first and second pulsed bremsstrahlung beams 416, 418 produced by the first and second conversion targets 408, 410 are respectively directed in respective first and second directions. The first collimator 420, generally, includes an elongate, narrow opening (e.g., a slot) through which a portion of the first pulsed bremsstrahlung beam 416 passes to create a third pulsed bremsstrahlung beam 424 having a beam shape suitable for cargo container inspection. Preferably, the third pulsed bremsstrahlung beam 424 has a fan shape upon exiting the first collimator 420. The first collimator 420 is, typically, mounted to and/or integrated into a wall 426 separating a first accelerator room 428 in which the first accelerator 404 and first conversion target 408 reside and an inspection room 430 through which cargo containers 402 are moved and exposed to the third pulsed bremsstrahlung beam 424 exiting the first collimator 420. During inspection, the cargo containers 402 are, generally, moved in a linear direction of travel that is perpendicular to the longitudinal axis 432 of the first accelerator 404. As a consequence, the third pulsed bremsstrahlung beam 424 is directed predominantly at a first side of each cargo container 402 such that a substantial portion of it passes through the cargo container 402-(and the contents thereof) and through a second, opposing side of each cargo container 402. Notably, the first accelerator room 428 is, generally, located horizontally adjacent to the inspection room 430 at substantially the same elevation.

The second collimator 422, generally, includes an elongate, narrow opening (e.g., a slot) through which a portion of the second pulsed bremsstrahlung beam 418 passes to create a fourth pulsed bremsstrahlung beam 434 having a beam shape suitable for cargo container inspection. Preferably, the fourth pulsed bremsstrahlung beam 434 has a fan shape upon exiting the second collimator 422. The second collimator 422 is, typically, mounted to and/or integrated into a wall 436 separating a second accelerator room 438 in which the second accelerator 406 and second conversion target 410 reside and the inspection room 430 through which cargo containers 402 are moved and exposed to the fourth pulsed bremsstrahlung beam 434 exiting the second collimator 422. During inspection, the cargo containers 402 are, generally, moved in a linear direction of travel that is perpendicular to the longitudinal axis 440 of the second accelerator 406. Notably, the second accelerator room 438 is located vertically adjacent to the inspection room 430 at an elevation above the elevation of the inspection room 430. As a consequence, the second accelerator 406 and second conversion target 410 located, generally, above the inspection room 430 and above cargo containers 402 as they travel through the inspection room 430. Thus, the fourth pulsed bremsstrahlung beam 434 is directed in a predominantly downward direction such that the predominant portion of the fourth pulsed bremsstrahlung beam 434 passes initially through the top, or roof, of a cargo container 402 being inspected, through the contents of the cargo container 402, and through the bottom of the cargo container 402.

The non-intrusive inspection system 400 additionally comprises a detector system 442 having a first detector array 444 with a plurality of detectors 446 that are each operable to receive a portion of the third pulsed bremsstrahlung beam 424 after it passes through a cargo container 402 and to produce an electrical signal representative thereof. The first detector array 444, generally, has an "L" shape with a first portion 448 of the first detector array 444 being oriented in a substantially vertical plane perpendicular to the direction of the first accelerator's longitudinal axis 432 and substantially parallel to and adjacent a side of a cargo container 402 as the cargo container 402 travels through the inspection room 430. The first detector array 444 also has a second portion 450 with a plurality of detectors 452 that is oriented in a substantially horizontal plane perpendicular to the substantially vertical plane of the first portion 448 thereof such that the second portion 450 of the first detector array 444 extends at least partially below a cargo container 402 as the cargo container 402 travels through the inspection room 430. In order to enable the reception of portions of the third pulsed bremsstrahlung beam 424 that may pass through the top, or roof, of a cargo container 402, some of the individual detectors 452 of the second portion 450 of the first detector array 444 are oriented in a direction toward, or facing, the first collimator 420 as opposed to being oriented in a downward direction perpendicular to the horizontal plane of the second portion 450 of the first detector array 444 and perpendicular to the top of a cargo container 402 passing through the inspection room 430.

The detector system 442 further comprises a second detector array 454 having a plurality of detectors 456 that are each operable to receive a portion of the fourth pulsed bremsstrahlung beam 434 after it passes through a cargo container 402 and to produce an electrical signal representative thereof. The plurality of detectors 456 of the second detector array 454 are, generally, oriented in a substantially horizontal plane perpendicular to the direction of the second accelerator's longitudinal axis 440 such that the detectors 456 of the second detector array 454 reside substantially beneath the bottoms of cargo containers 402 as they are moved through the inspection room 430 by a conveyor 458 located in the floor of the inspection room 430.

It should be noted that because the non-intrusive inspection system 400 exposes a cargo container 402 to two pulsed bremsstrahlung (or x-ray) beams 424, 434 and has first and second detector arrays 444, 454 that are populated with detectors 446, 456 for detection and imaging capability in two planes (i.e., the vertical plane of the first portion 448 of the first detector array 444 and the horizontal plane of the second detector array 454), the non-intrusive inspection system 400 of the fourth exemplary embodiment is, typically, categorized as a "dual-plane inspection system".

Although not described in detail herein, the non-intrusive inspection system 400 further comprises various other components, including an imaging subsystem having data communication equipment and computer systems with appropriate software, that are configured to receive and transform electrical signals produced by the first and second detector arrays 444, 454 into images of the contents of a cargo container 402 for display to inspection system operators. The images produced by the imaging subsystem, generally, comprise two dimensional views of the contents of a cargo container 402 with the first being taken from the perspective of a side thereof such that a first image may extend between the container's ends and the container's top and bottom, and with the second being taken from the perspective of the bottom thereof such that a second image may extend between the container's ends and the container's sides.

The non-intrusive inspection system 400 further comprises a material discrimination subsystem that is connected to and receives electrical signals from the first and second detector arrays 444, 454 and that identifies, or discriminates, various materials present in the contents of a cargo container 402. Such material discrimination is possible because the non-intrusive inspection system 400 utilizes two pulsed beams of accelerated electrons that each, respectively, include pulses of electrons having first and second energy levels and exposes a cargo container 402 to pulsed bremsstrahlung beams 424, 434 each having two different energy spectra (i.e., due to the creation of the pulsed bremsstrahlung beams 424, 434 from pulses of electrons having first and second energy levels). The material discrimination subsystem is operable to receive data corresponding to the x-ray pulses that pass through the opposing sides and top and bottom of a cargo container 402 in the form of electrical signals received from the detector arrays 444, 454. The material discrimination subsystem is further operable to analyze the received data and, using methods known to one of ordinary skill in the art, to identify and/or discriminate the materials present in the contents of a cargo container 402.

Figure 11:
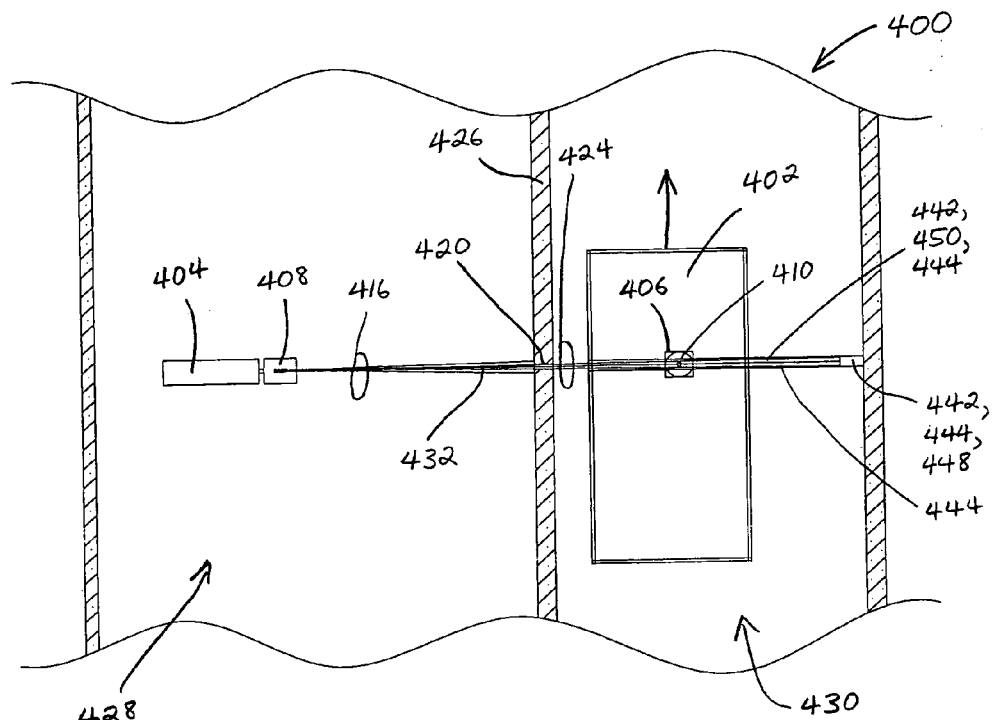
FIG. 11 displays a top plan, schematic sectional view of the non-intrusive inspection system of FIG. 10 in accordance with the fourth exemplary embodiment of the present invention.

FIG. 11 displays a top plan, schematic sectional view of the non-intrusive inspection system 400 of FIG. 10 in accordance with the fourth exemplary embodiment of the present invention. As seen in FIG. 11, the first accelerator 404 is positioned such that the first accelerator's longitudinal axis 432 is perpendicular to the first portion 448 of the first detector array 444 and perpendicular to the direction of travel of the cargo container 402 through the inspection room 430. The second accelerator 406 is positioned such that it is above the cargo container 402 with the second accelerator's longitudinal axis 440 being perpendicular to the second detector array 454.

In operation, the first and second accelerators 404, 406 of the non-intrusive inspection system 400 are appropriately controlled to produce first and second pulsed beams of accelerated electrons impinging, respectively, on the first and second conversion targets 408, 410 that alternately include pulses of electrons having first and second energy levels. Generally, the first and second energy levels of the pulses of electrons from the first accelerator 404 are the same as the first and second energy levels of the pulses of electrons from the second accelerator 406. Because the pulses of electrons in the pulsed beams of accelerated electrons impinging on the first and second conversion targets 408, 410 alternate between first and second energy levels, each of the pulsed bremsstrahlung beams 416, 418 produced by the first and second conversion targets 408, 410 include two different energy spectra corresponding to the first and second energy levels which enable discrimination of the materials present in the contents of, or objects within, a cargo container 402.

More specifically, at a first time, the first and second accelerators 404, 406 are operated to generate pulses of electrons having a first energy level that are directed toward the first and second conversion targets 408, 410 by respective first and second vacuum electron beam guides 412, 414. Upon receiving the pulses of electrons having a first energy level, the first and second conversion targets 408, 410 convert the received pulses of electrons into bremsstrahlung (or x-rays) having first energy spectra corresponding to the first energy level of the pulses of electrons from the first and second accelerators 404, 406. The produced bremsstrahlung is then emitted from the first and second conversion targets 408, 410 in respective directions toward the respective first and second collimators 420, 422.

At a second time subsequent to the first time, the first and second accelerators 404, 406 are operated to generate pulses of electrons having a second energy level that are directed toward the first and second conversion targets 408, 410 by respective first and second vacuum electron beam guides 412, 414. Upon receiving the pulses of electrons having a second energy level, the first and second conversion targets 408, 410 convert the received pulses of electrons into bremsstrahlung (or x-rays) having second energy spectra corresponding to the second energy level of the pulses of electrons from the first and second accelerators 404, 406. The produced bremsstrahlung is then emitted from the first and second conversion targets 408, 410 in respective directions toward the respective first and second collimators 420, 422.

Operation of the first and second accelerators 404, 406 continues in such an alternating manner during operation of the non-intrusive inspection system 400 to produce, when integrated over time, the pulsed beams of accelerated electrons having pulses of electrons with alternating first and second energy levels that impinge on the first and second conversion targets 408, 410. Similarly, operation of the first and second conversion targets 408, 410 continues in such an alternating manner to produce, when integrated over time, the first and second pulsed bremsstrahlung (i.e., x-ray) beams 416, 418 having first and second energy spectra that are, respectively, directed toward the first and second collimators 420, 422. As the first and second pulsed bremsstrahlung beams 416, 418 pass, respectively, through the elongate, narrow openings of the first and second collimators 420, 422, the first and second pulsed bremsstrahlung beams 416, 418 are shaped to produce the third and fourth pulsed bremsstrahlung beams 424, 434 that exit the first and second collimators 420, 422 and impinge upon a cargo container 402 being moved through the inspection room 430. The third pulsed bremsstrahlung beam 424 passes through the opposing sides, or walls, and a portion of the top of the cargo container 402 and through objects present within the cargo container 402 such that different portions of the beam 424 impinge upon different detectors 446 of the first detector array 444. The fourth pulsed bremsstrahlung beam 434 passes through the top, bottom, and opposing sides, or walls, of the cargo container 402 and through objects present within the cargo container 402 such that different portions of the beam 434 impinge upon different detectors 452 of the second detector array 450 and different detectors 446 of the first detector array 444.

The detectors 446, 452, upon receiving respective portions of the third and fourth pulsed bremsstrahlung beams 424, 434, each produce an electrical signal representative of the portion of the third and fourth pulsed bremsstrahlung beams 424, 434 received thereby. The detector system 442 communicates the produced electrical signals, or an equivalent thereof, to the imaging and material discrimination subsystems for the generation of two-dimensional images representative of the contents of (or, objects present within) the cargo container 402 as viewed from different directions and for the discrimination and identification of materials present in such objects.

Figure 12:
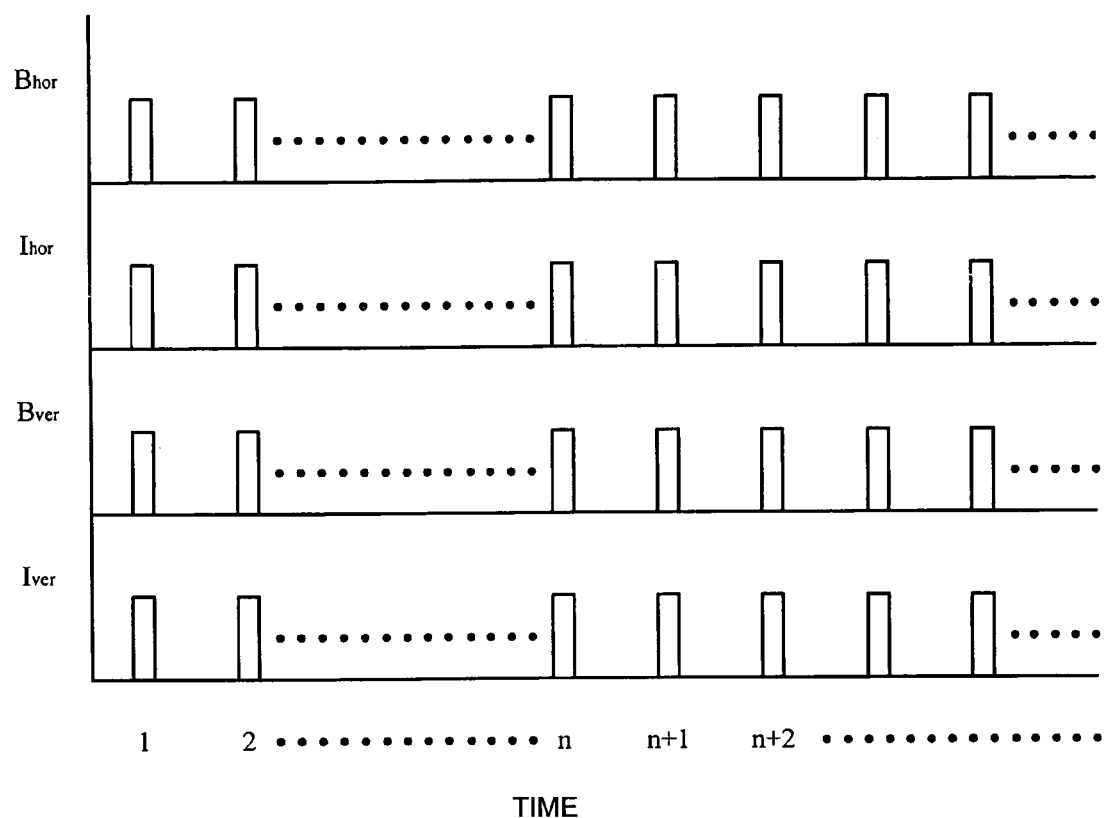
FIG. 12 displays a timing diagram illustrating the timing of various pulses during operation of the non-intrusive inspection system of FIG. 10 in accordance with the fourth exemplary embodiment of the present invention.

FIG. 12 displays a timing diagram illustrating the relative timing of the alternating electron beam current pulses of the pulsed beam of accelerated electrons impinging on the conversion targets 408, 410 and the alternating pulses of the pulsed bremsstrahlung beams 416, 418 in accordance with the fourth exemplary embodiment of the present invention. As illustrated in FIG. 12, at a first time denoted by the number "1" on the horizontal time axis of the timing diagram, the first and second accelerators 404, 406 emit electron beam current pulses having a first energy level. Therefore, at the first time, the pulsed beam of accelerated electrons impinging on the conversion targets 408, 410 comprise electron beam current pulses from the first accelerator 404 (i.e., denoted by a positive beam current, $I_{hor}$) and from the second accelerator 406 (i.e., denoted by a positive beam current, $I_{ver}$). Consequently, at the first time, the pulsed bremsstrahlung beams 416, 418 comprise bremsstrahlung pulses having a first energy spectra (i.e., denoted by the pulses on the $B_{hor}$ and $B_{ver}$ axes).

At a second time denoted by the number "2" on the horizontal time axis of the timing diagram, the first and second accelerators 404, 406 emit electron beam current pulses having a second energy level. Therefore, at the second time, the pulsed beam of accelerated electrons impinging on the conversion targets 408, 410 comprise electron beam current pulses from the first accelerator 404 (i.e., denoted by a positive beam current, $I_{hor}$) and from the second accelerator 406 (i.e., denoted by a positive beam current, $I_{ver}$). Consequently, at the second time, the pulsed bremsstrahlung beams 416, 418 comprise bremsstrahlung pulses having a second energy spectra (i.e., denoted by the pulses on the $B_{hor}$ and $B_{ver}$ axes) different from the first energy spectra. As additionally illustrated in FIG. 12, the timing of pulses at the first and second times (i.e., "1" and "2") is repeated at respectively successive times with the beam currents and energy spectra corresponding to the first time being repeated at successive odd numbered times and the beam currents and energy spectra corresponding to the second time being repeated at successive even numbered times.

FIG. 13 displays a side elevation, schematic sectional view of a non-intrusive inspection system 500 for inspecting the contents of a cargo container 502 in accordance with a fifth exemplary embodiment of the present invention. The non-intrusive inspection system 500 comprises an accelerator 504, a first turning magnet 506 (also sometimes referred to as a "first kicker magnet 506"), and a first conversion target 508. Generally, the accelerator 504 comprises a pulse-type, electron accelerator that is operable to produce, or emit, a pulsed beam of accelerated electrons including pluralities of electron pulses having alternating first and second energy levels. The output port of the accelerator 504 and the first turning magnet 506 are connected by a first vacuum electron beam guide 510 which is adapted to guide the pulsed beam of accelerated electrons from the output port of the accelerator 504 to the first turning magnet 506. The first turning magnet 506 is adapted to turn the pulsed beam of accelerated electrons emitted by the accelerator 504 (and received via first vacuum electron beam guide 510) when an energizing pulse of electrical current is applied thereto and to allow the pulsed beam of accelerated electrons to pass therethrough without turning when no energizing pulse of current is applied thereto. The first turning magnet 506 and the first conversion target 508 are connected by a second vacuum electron beam guide 512 that is configured to direct the pulsed beam of accelerated electrons from the first turning magnet 510 to the first conversion target 508.

The first conversion target 508 is operable to receive pulses of electrons of the pulsed beam of accelerated electrons from the second vacuum electron beam guide 512 and to convert the received pulses of electrons into a first pulsed bremsstrahlung (i.e., x-ray) beam 514 that is emitted, or output, from the conversion target 508 and directed in a direction toward a first collimator 516. Generally, the first pulsed bremsstrahlung beam 514 includes first and second energy spectra corresponding, respectively, to the first and second energy level of the pulses of electrons that are present in the pulsed beam of accelerated electrons emitted by the accelerator 504.

The first collimator 516, typically, includes an elongate, narrow opening (e.g., a slot) through which a portion of the first pulsed bremsstrahlung beam 514 passes to produce a second pulsed bremsstrahlung beam 518 having a beam shape suitable for cargo container inspection. Preferably, the second pulsed bremsstrahlung beam 518 has a fan shape upon exiting the first collimator 516. The first collimator 516 is, generally, mounted to and/or integrated into a wall 520 separating an accelerator room 522 in which the accelerator 504, first turning magnet 506, and first conversion target 508 reside and an inspection room 524 through which cargo containers 502 are moved and exposed to the second pulsed bremsstrahlung beam 518 exiting the first collimator 516. During inspection, the cargo containers 502 are, generally, moved in a linear direction of travel that is perpendicular to the direction of the longitudinal axis 525 of the accelerator 504 such that the second pulsed bremsstrahlung beam 518 is predominantly directed at and impinges on a side of each cargo container 502 while moving through the inspection room 524.

The non-intrusive inspection system 500 also comprises a second turning magnet 526, a third turning magnet 528, and a second conversion target 530. The second turning magnet 526 (also sometimes referred to as a "second kicker magnet 526") is, typically, located in a first auxiliary room 532 substantially beneath the accelerator room 522 at a position elevationally below tile first turning magnet 506. First and second triplets 534, 536 (e.g., sets of focusing lenses) are interposed between the first and second turning magnets 506, 526 to refocus the pulsed beam of accelerated electrons emitted by the accelerator 504. The first triplet 534 is connected to the first turning magnet 506 by a third vacuum electron beam guide 538 which is adapted to guide the pulsed beam of accelerated electrons from the first turning magnet 510 to the input of the first triplet 534. A fourth vacuum electron beam guide 540 is connected to the output of the first triplet 534 and to the input of the second triplet 536, and is configured to direct the pulsed beam of accelerated electrons from the first triplet 534 to the second triplet 536. The output of the second triplet 536 is connected to the input of the second turning magnet 526 by a fifth vacuum electron beam guide 542 that is adapted to guide the pulsed beam of accelerated electrons from the second triplet 536 to the second turning magnet 526. The second turning magnet 526 is adapted to turn the pulsed beam of accelerated electrons emitted by the accelerator 504 (and received via fifth vacuum electron beam guide 542) toward the third turning magnet 528 when an energizing pulse of electrical current is applied thereto (i.e., which may occur continuously or only when a similar energizing pulse of electrical current is applied to the first turning magnet 506).

The third turning magnet 528 (also sometimes referred to as a "third kicker magnet 528") is, typically, located in a second auxiliary room 544 substantially beneath the inspection room 524 at a position having an elevation substantially equal to the elevation of the position of the second turning magnet 526. Third and fourth triplets 546, 548 (e.g., sets of focusing lenses) are interposed between the second and third turning magnets 526, 528 to refocus the pulsed beam of accelerated electrons emitted by the accelerator 504. The third triplet 546 is connected to the second turning magnet 526 by a sixth vacuum electron beam guide 550 which is adapted to guide the pulsed beam of accelerated electrons from the second turning magnet 526 to the input of the third triplet 546. A seventh vacuum electron beam guide 552 is connected to the output of the third triplet 546 and to the input of the fourth triplet 548, and is configured to direct the pulsed beam of accelerated electrons from the third triplet 546 to the fourth triplet 548. The output of the fourth triplet 548 is connected to the input of the third turning magnet 528 by an eighth vacuum electron beam guide 554 that is adapted to guide the pulsed beam of accelerated electrons from the fourth triplet 548 to the third turning magnet 528. The third turning magnet 528 is adapted to turn the pulsed beam of accelerated electrons emitted by the accelerator 504 (and received via eighth vacuum electron beam guide 554) toward the second conversion target 530 when an energizing pulse of electrical current is applied thereto (i.e., which may occur continuously or only when a similar energizing pulse of electrical current is applied to the first and second turning magnets 506, 528).

The second conversion target 530 is connected to the third turning magnet 528 by a ninth vacuum electron beam guide 556 extending therebetween that is adapted to guide pulses of electrons of the pulsed beam of accelerated electrons toward the second conversion target 530. The second conversion target 530 is operable to receive pulses of electrons of the pulsed beam of accelerated electrons from the ninth vacuum electron beam guide 556 and to convert the received pulses of electrons into a third pulsed bremsstrahlung (i.e., x-ray) beam 558 that is output from the second conversion target 530 and directed toward a second collimator 560. Generally, the third pulsed bremsstrahlung beam 558 includes first and second energy spectra corresponding to the first and second energy levels of the pulses of electrons that are present in the pulsed beam of accelerated electrons emitted by the accelerator 504.

The second collimator 560, typically, includes an elongate, narrow opening (e.g., a slot) through which a portion of the third pulsed bremsstrahlung beam 558 passes to produce a fourth pulsed bremsstrahlung beam 562 having a beam shape suitable for cargo container inspection. Preferably, the fourth pulsed bremsstrahlung beam 562 has a fan shape upon exiting the second collimator 560. The second collimator 560 is, generally, mounted to and/or integrated into a wall 564 separating the second auxiliary room 544 in which the third turning magnet 528 and second conversion target 530 reside and the inspection room 524 through which cargo containers 502 are moved and exposed to the fourth pulsed bremsstrahlung beam 562 exiting the second collimator 560. During inspection, the cargo containers 502 are, generally, moved by a conveyor 565 in a linear direction of travel that is perpendicular to a vertical axis 566 extending through the second conversion target 530 such that the fourth pulsed bremsstrahlung beam 562 is directed, generally, at and impinges on the bottom of each cargo container 502 during movement thereof through the inspection room 524.

The non-intrusive inspection system 500 additionally comprises a detector system 568 having a detector array 570 with a plurality of detectors 572 that are each operable to receive a portion of the second and fourth pulsed bremsstrahlung beams 518, 562 after they pass through a cargo container 502 and produce electrical signals representative thereof. The detector array 570, generally, has an "L" shape with a first portion 574 thereof being oriented in a substantially vertical plane perpendicular to the longitudinal axis 525 of the accelerator 504 and substantially parallel to and adjacent a side of a cargo container 502 as the cargo container 502 travels through the inspection room 524. The detector array 570 also has a second portion 576 that is oriented in a substantially horizontal plane perpendicular to the substantially vertical plane of the first portion 574 thereof and perpendicular to the vertical axis 566 extending through the second conversion target 530 such that the second portion 576 of the detector array 570 extends at least partially above a cargo container 502 as the cargo container 502 travels through the inspection room 524.

In order to enable the reception of portions of the second pulsed bremsstrahlung beam 518 that may pass through the top, or roof, of a cargo container 502, some of the individual detectors 572 of the second portion 576 of the detector array 570 are slightly turned in a direction somewhat toward, or facing, the first collimator 516 as opposed to being oriented entirely in a downward direction perpendicular to the horizontal plane of the second portion 576 of the detector array 570. Similarly, in order to enable the reception of portions of the fourth pulsed bremsstrahlung beam 562 that may pass through a side of a cargo container 502, some of the individual detectors 572 of the first portion 574 of the detector array 570 are slightly turned in a direction somewhat toward, or facing, the second collimator 560 as opposed to being oriented entirely in a direction perpendicular to the vertical plane of the first portion 574 of the detector array 570. It should be noted that because the non-intrusive inspection system 500 exposes a cargo container 502 to two pulsed bremsstrahlung beams 518, 562 and has a detector array 570 that is fully populated with detectors 572 for detection and imaging capability in two planes (i.e., the vertical plane of the first portion 574 of the detector array 570 and the horizontal plane of the second portion 576 of the detector array 570), the non-intrusive inspection system 500 of the fifth exemplary embodiment is, typically, categorized as a "dual-plane inspection system".

Although not described in detail herein, the non-intrusive inspection system 500 further comprises various other components, including an imaging subsystem having data communication equipment and computer systems with appropriate software, that are configured to receive and transform electrical signals produced by the detector array 570 into images of the contents of a cargo container 502 for display to inspection system operators. The images produced by the imaging subsystem, generally, comprise two-dimensional views of the contents of a cargo container 502 taken in the first view from the perspective of a side thereof such that a first image may extend between the container's ends and the container's top and bottom, and taken in the second view from the perspective of the bottom thereof such that a second image may extend between the container's ends and the container's sides.

The non-intrusive inspection system 500 further comprises a material discrimination subsystem that is connected to and receives electrical signals from the detector array 570, and that identifies, or discriminates, various materials present in the contents of a cargo container 502. Such material discrimination is possible because the non-intrusive inspection system 500 utilizes a single accelerator 504 that produces a pulsed beam of accelerated electrons having first and second energy levels and exposes a cargo container 502 to pulsed bremsstrahlung beams 518, 562 each having first and second energy spectra (i.e., due to the creation of the pulsed bremsstrahlung beams 518, 562 from the pulsed beam of electrons having first and second energy levels). The material discrimination subsystem is operable to receive data corresponding to the x-ray pulses that pass through the opposing sides and top and bottom of a cargo container 502 in the form of electrical signals received from the detector array 570. The material discrimination subsystem is further operable to analyze the received data and, using methods known to one of ordinary skill in the art, to identify and/or discriminate the materials present in the contents of a cargo container 502.

FIG. 14 displays a top plan, schematic sectional view of the non-intrusive inspection system 500 of FIG. 13 in accordance with the fifth exemplary embodiment of the present invention. As seen in FIG. 14, the accelerator 504 is positioned such that the accelerator's longitudinal axis 525 is perpendicular to the first portion 574 of the detector array 570 and perpendicular to the direction of travel of the cargo container 502 through the inspection room 524. Notably, the second turning magnet 526 is directly beneath the first turning magnet 506.

In operation, the accelerator 504 and the first, second and third turning magnets 506, 526, 528 of the cargo container non-intrusive inspection system 500 are appropriately controlled to produce a pulsed beam of accelerated electrons with odd numbered pairs of consecutive pulses of electrons thereof being directed toward the first conversion target 508 and even numbered pairs of consecutive pulses of electrons thereof being directed toward the second conversion target 530. The pulses of each pair of electrons produced by the accelerator 504 alternatively have different first and second energy levels and, as a consequence, the first and second pulsed bremsstrahlung beams 518, 562 generated by the first and second conversion targets 508, 530 each include different first and second energy spectra. Because two pulsed bremsstrahlung beams 518, 562 are employed with a detector array 570 capable of detecting portions of the pulsed bremsstrahlung beams 518, 562, in horizontal and vertical planes, that pass through a cargo container 502, the non-intrusive inspection system 500 produces two-dimensional views of the cargo container 502 from different directions that, essentially, allow three-dimensional viewing of the contents of the cargo container 502. Further, because the two pulsed bremsstrahlung beams 518, 562 each have first and second energy spectra corresponding to the first and second energy levels of the pulses of electrons produced by the accelerator 504, the non-intrusive inspection system 500 can distinguish between and identify materials present in the contents of, or objects in, a cargo container 502.

More specifically, at a first pair of times, the accelerator 504 is operated to generate a first pair of electron pulses having a first pulse with a first energy level and a second pulse with a second energy level. The first pair of pulses is directed toward the first turning magnet 506 by the first vacuum electron beam guide 510. At the first pair of times, no energizing signal pulse (i.e., electrical current) is concurrently applied to the first turning magnet 506, thereby placing the first turning magnet 506 into a de-energized state and allowing the first pair of pulses of electrons from the first accelerator 504 to pass through the first turning magnet 506 with their direction unchanged and on toward the conversion target 508 through the second vacuum electron beam guide 512. In response to receiving the first pulse of electrons of the first pair of pulses of electrons, the conversion target 508 converts the first pulse of electrons into a pulse of bremsstrahlung (i.e., a pulse of first bremsstrahlung beam 514) having a first energy spectra corresponding to the first energy level of the first pulse of electrons from the first accelerator 504. Then, the conversion target 508 converts the second pulse of electrons into a pulse of bremsstrahlung (i.e., a pulse of first bremsstrahlung beam 514) having a second energy spectra corresponding to the second energy level of the second pulse of electrons from the first accelerator 504. The produced pulses of bremsstrahlung are emitted from the conversion target 508 in a direction toward the first collimator 516 which shapes the pulses of bremsstrahlung to produce shaped pulses of bremsstrahlung (i.e., pulses of second bremsstrahlung beam 516) which impinge upon a side of a cargo container 502 being moved through the inspection room 524.

At a second pair of times, the accelerator 504 is operated to generate a second pair of electron pulses having a first pulse with a first energy level and a second pulse with a second energy level. The second pair of pulses is directed to the first turning magnet 506 by the first vacuum electron beam guide 510. At the second pair of times, an energizing signal pulse (i.e., electrical current) is concurrently applied to the first turning magnet 506 and to the second and third turning magnets 526, 528 (or, alternatively, energizing signal pulses (i.e., electrical current) may be continuously applied to the second and third turning magnets 526, 528), thereby placing the first turning magnet 506 into an energized state and allowing the second pair of electron pulses from the accelerator 504 to be turned by the first turning magnet 506 in a new direction toward the second turning magnet 526. After being turned by the first turning magnet 506, the second pair of electron pulses travels through the first and second triplets 534, 536 and the third, fourth and fifth vacuum electron beam guides 538, 540, 542 to the second turning magnet 526. While traveling through the first and second triplets 534, 536, the second pulse of electrons is re-focused to minimize dispersion of the electrons thereof.

Upon arriving at and passing through the energized second turning magnet 526, the second pair of electron pulses is turned by the second turning magnet 526 in a new direction toward the third turning magnet 528. The second pair of electron pulses then travels through the third and fourth triplets 546, 548 and the sixth, seventh, and eighth vacuum electron beam guides-550, 552, 554 to the third turning magnet 528. While traveling through the third and fourth triplets 546, 548, the second pair of electron pulses is once again re-focused to minimize dispersion of the electrons thereof.

After reaching the third turning magnet 528, the second pair of electron pulses is turned by the third turning magnet 528 in a new direction toward the second conversion target 530. The second pair of electron pulses then travels through the ninth vacuum electron beam guide 556 to the second conversion target 530. Upon receiving the second pair of electron pulses, the second conversion target 530 converts the received first pulse of the second pair of electron pulses into a first pulse of bremsstrahlung (i.e., a first pulse of the third pulsed bremsstrahlung beam 558) having a first energy spectra corresponding to the first energy level of the first pulse of the second pair of electron pulses emitted from the accelerator 504 (and, hence, to the first energy spectra of the first pulsed bremsstrahlung beam 514). Then, the second conversion target 530 converts the received second pulse of the second pair of electron pulses into a second pulse of bremsstrahlung (i.e., a second pulse of the third pulsed bremsstrahlung beam 558) having a second energy spectra corresponding to the second energy level of the second pulse of the second pair of electron pulses emitted from the accelerator 504 (and, hence, to the second energy spectra of the first pulsed bremsstrahlung beam 514). The produced pulses of bremsstrahlung are then emitted from the second conversion target 530 in a direction toward the second collimator 560 which shapes the pulses of bremsstrahlung to produce shaped pulses of bremsstrahlung (i.e., pulses of second pulsed bremsstrahlung beam 562) which-impinge upon the bottom of a cargo container 502 being moved through the inspection room 524.

Operation of the accelerator 504 and the first, second and third turning magnets 506, 526, 528 continues in an alternating manner during operation of the non-intrusive inspection system 500 to direct odd numbered pairs of pulses of electrons produced by the accelerator 504 toward the first conversion target 508 and even numbered pairs of pulses of electrons produced by the accelerator 504 toward the second conversion target 530. The second and fourth pulsed bremsstrahlung beams 518, 562 produced therefrom, as a consequence, comprise pairs of pulses of bremsstrahlung (or x-rays) that impinge, respectively, upon a side wall and bottom of a cargo container 504 at alternating times, thereby causing the detectors 572 of the detector array 574 to alternately produce electrical signals representative of the portions of the pairs of pulses of bremsstrahlung that pass through the contents of a cargo container 502 from a side or bottom thereof and strike the detectors 572. The detector system 570 communicates the produced electrical signals, or an equivalent thereof, to the imaging subsystem for the generation of respective two-dimensional images representative of the contents of (or, objects present within) the cargo container 502 when viewed from a side and bottom thereof.

Figure 15:
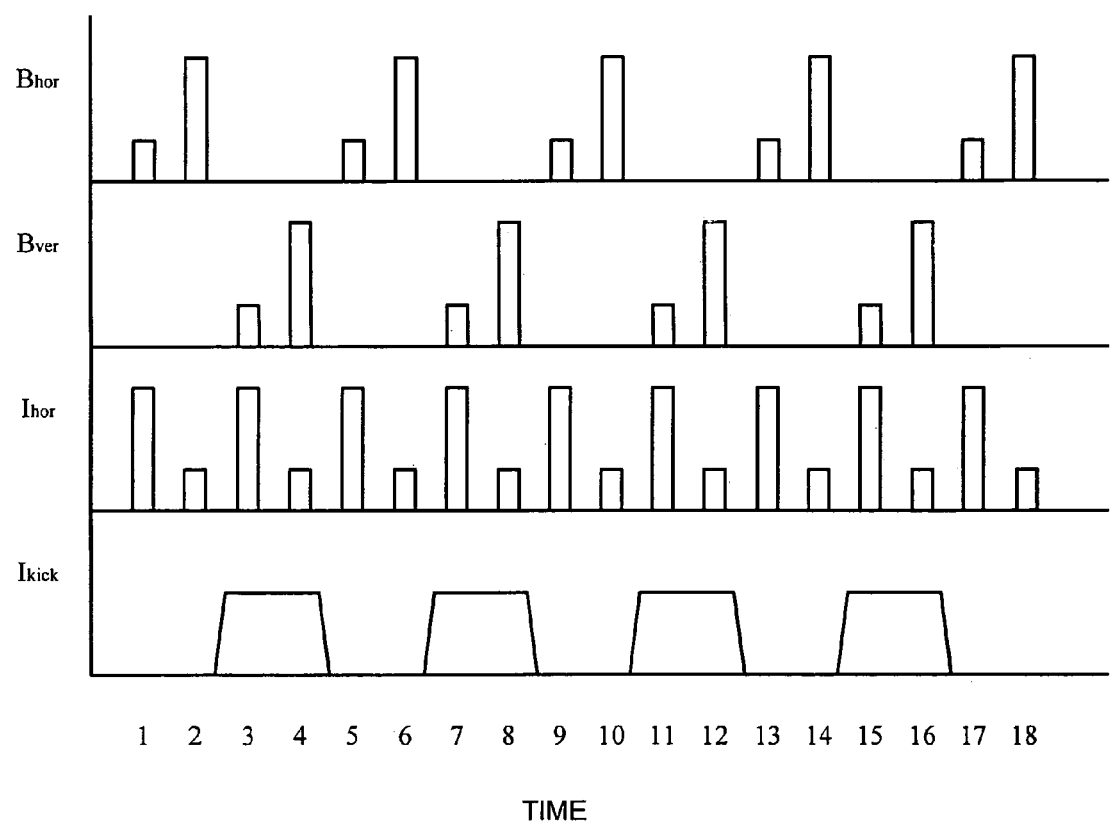
FIG. 15 displays a timing diagram illustrating the timing of various pulses during operation of the non-intrusive inspection system of FIG. 13 in accordance with the fifth exemplary embodiment of the present invention.

FIG. 15 displays a timing diagram illustrating the relative timing of the electron beam current pulses of the pulsed beam of accelerated electrons alternatingly impinging on the conversion targets 508, 530, the alternating bremsstrahlung pulses of the second and fourth pulsed bremsstrahlung beams 518, 562, and the energizing signals applied to the first, second and third turning magnets 506, 526, 528, in accordance with the fifth exemplary embodiment of the present invention. As illustrated in FIG. 15, at a first pair of times denoted by the numbers "1" and "2" on the horizontal time axis of the timing diagram, no energizing signal (i.e., electrical current) is applied to the first, second and third turning magnets 506, 526, 528 as indicated by the magnet current, $I_{kick}$, having a zero value. At the first pair of times and by virtue of no energizing signal being applied to the first, second and third turning magnets 506, 526, 528, the accelerator 504 emits a pair of electron beam current pulses that pass through the first turning magnet 506 without being turned. Therefore, at the first pair of times, the electron beam current pulses emitted from the accelerator 504 impinge on the first conversion target 308, causing the generation of pulses of bremsstrahlung of the first and second pulsed bremsstrahlung beams 314, 318 having first and second energy spectra (i.e., denoted by a pair of pulses on the $B_{hor}$ axis) corresponding to the first and second energy levels of the electron beam current pulses.

At a second pair of times denoted by the numbers "3" and "4" on the horizontal time axis of the timing diagram, an energizing signal (i.e., current) is applied to the first, second and third turning magnets 506, 526, 528 as indicated by the magnet current, $I_{kick}$, having a non-zero value. At the second pair of times and by virtue of an energizing signal being applied to the first, second and third turning magnets 506, 526, 528, the accelerator 504 emits a pair of electron beam current pulses that pass through the first turning magnet 506 and is turned toward the second turning magnet 526. Therefore, at the second pair of times, the electron beam current pulses emitted from the accelerator 504 impinge on the second conversion target 530, causing the generation of pulses of bremsstrahlung of the third and fourth pulsed bremsstrahlung beams 558, 562 having first and second energy spectra (i.e., denoted by the pair of pulses on the $B_{ver}$ axis) corresponding to the first and second energy levels of the electron beam current pulses. As additionally illustrated in FIG. 15, the timing of pulses at the first and second pair of times is repeated at respectively successive pairs of times with the beam currents and energy spectra corresponding to the first pair of times being repeated at successive odd numbered pairs of times and the beam currents and energy spectra corresponding to the second pair of times being repeated at successive even numbered pairs of times.

Figure 16:
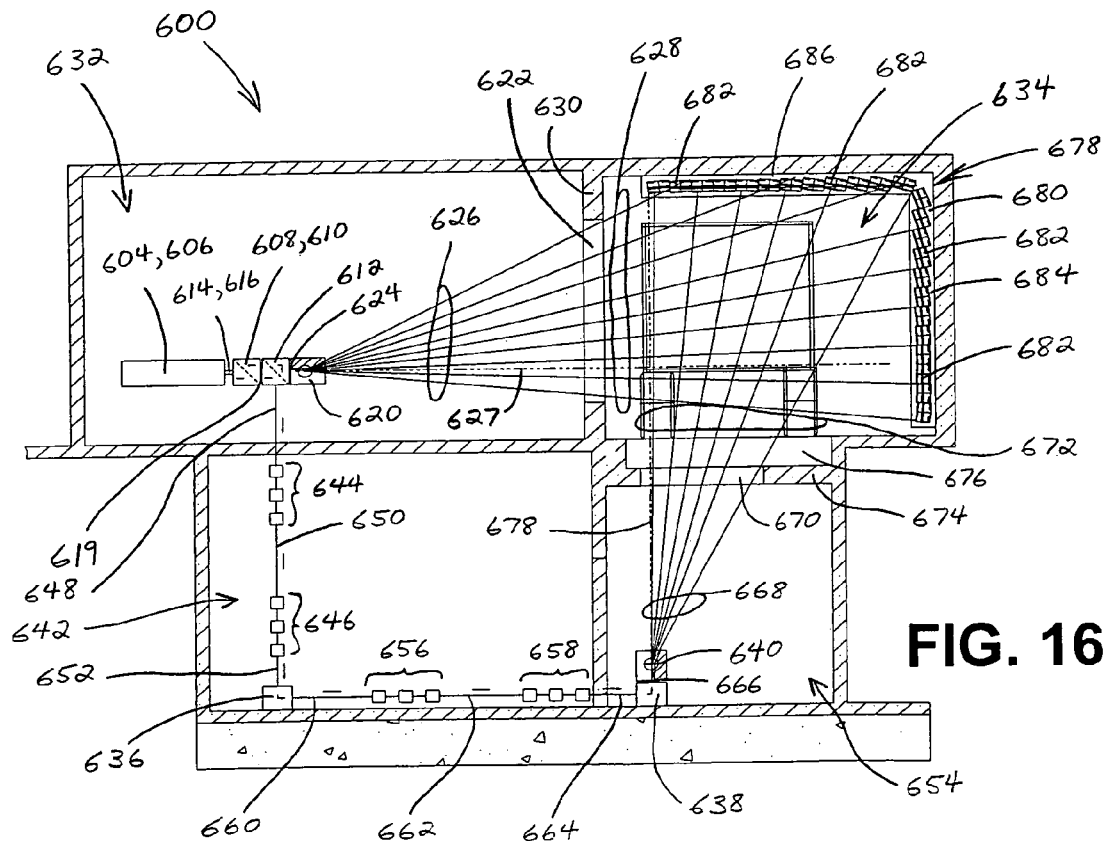
FIG. 16 displays a side elevation, schematic sectional view of a non-intrusive inspection system for inspecting the contents of a cargo container in accordance with a sixth exemplary embodiment of the present invention.

FIG. 16 displays a side elevation, schematic sectional view of a non-intrusive inspection system 600 for inspecting the contents of a cargo container 602 in accordance with a sixth exemplary embodiment of the present invention. The non-intrusive inspection system 600 comprises first and second accelerators 604, 606 and first, second and third turning magnets 608, 610, 612 (also sometimes referred to herein as "kicker magnets 608, 610, 612"). The first accelerator 604 comprises a pulse-type, electron accelerator that is operable to produce, or emit, a pulsed beam of accelerated electrons in a first direction including a plurality of electron pulses having a first energy level. The second accelerator 606 comprises a pulse-type, electron accelerator that is operable to produce, or emit, a pulsed beam of accelerated electrons in a second direction including a plurality of electron pulses having a second energy level.

The first and second turning magnets 608, 610 are connected, respectively, to the output ports of the first and second accelerators 604, 606 by vacuum electron beam guides 614, 616 which are adapted to guide respective pulsed beams of accelerated electrons from the output ports of the first and second accelerators 604, 606 to the first and second turning magnets 608, 610. The first turning magnet 608 is connected to the second turning magnet 610 by vacuum electron beam guide 618 which is configured to guide a pulsed beam of accelerated electrons from the second turning magnet 610 to the first turning magnet 608. The second turning magnet 610 is adapted to turn the pulsed beam of accelerated electrons emitted by the second accelerator 606 in a new direction toward the first turning magnet 608 when an energizing pulse is applied to the second turning magnet 610. The first turning magnet 608 is adapted to turn the pulsed beam of accelerated electrons emitted by the second accelerator 606 (and received from the second turning magnet 610) in a new direction toward the third turning magnet 612 when an energizing pulse is applied to the first turning magnet 608.

The third turning magnet 612 is connected to the first turning magnet 608 by vacuum electron beam guide 619 which is adapted to guide a pulsed beam of accelerated electrons from the first turning magnet 608. The third turning magnet 612 is operable to turn a pulsed beam of accelerated electrons (i.e., received from the first turning magnet 608) in a new direction toward the fourth turning magnet 636 (described below) when an energizing pulse (i.e., electrical current) is applied to the third turning magnet 612.

The non-intrusive inspection system 600 also comprises a first conversion target 620 and a first collimator 622. The first conversion target 620 is connected, via vacuum electron beam guide 624, to the third turning magnet 612. The vacuum electron beam guide 624 is adapted to direct a pulsed beam of accelerated electrons from the third turning magnet 612 to the first conversion target 620. The conversion target 620 is operable to receive pulses of electrons of the pulsed beam of accelerated electrons from vacuum electron beam guide 624 and to convert the received pulses of electrons into a first pulsed bremsstrahlung (or x-ray) beam 626 that is output from the first conversion target 620 and directed toward the first collimator 622. Generally, the first pulsed bremsstrahlung beam 626 includes energy spectra corresponding to the first and second energy levels of the respective pulses of electrons emitted by the first and second accelerators 604, 606 that are present in the pulsed beam of accelerated electrons.

The first collimator 622, generally, includes an elongate, narrow opening (e.g., a slot) through which a portion of the first pulsed bremsstrahlung beam 626 passes to create a second pulsed bremsstrahlung beam 628 having a beam shape suitable for cargo container inspection. Preferably, the second pulsed bremsstrahlung beam 628 has a fan shape upon exiting the first collimator 622. The first collimator 622 is, typically, mounted to and/or integrated into a wall 630 separating an accelerator room 632 in which the first and second accelerators 604, 606, first, second and third turning magnets 608, 610, 612, and first conversion target 620 reside and an inspection room 634 through which cargo containers 602 are moved and exposed to the second pulsed bremsstrahlung beam 628 exiting the first collimator 622. During inspection, the cargo containers 602 are, generally, moved in a linear direction of travel that is perpendicular to the direction of the longitudinal axis 627 of the first accelerator 604 such that the second pulsed bremsstrahlung beam 628 is predominantly directed at and impinges on a side of each cargo container 602 while moving through the inspection room 634.

The non-intrusive inspection system 600 also comprises a fourth turning magnet 636, a fifth turning magnet 638, and a second conversion target 640. The fourth turning magnet 636 (also sometimes referred to as a "fourth kicker magnet 636") is, typically, located in a first auxiliary room 642 substantially beneath the accelerator room 632 at a position elevationally below the third turning magnet 612. First and second triplets 644, 646 (e.g., sets of focusing lenses) are interposed between the third and fourth turning magnets 612, 636 to refocus the pulsed beams of accelerated electrons emitted by the first and second accelerators 604, 606. The first triplet 644 is connected to the third turning magnet 612 by a vacuum electron beam guide 648 which is adapted to guide the pulsed beam of accelerated electrons from the third turning magnet 612 to the input of the first triplet 644. A vacuum electron beam guide 650 is connected to the output of the first triplet 644 and to the input of the second triplet 646, and is configured to direct the pulsed beam of accelerated electrons from the first triplet 644 to the second triplet 646. The output of the second triplet 646 is connected to the input of the fourth turning magnet 636 by a vacuum electron beam guide 652 that is adapted to guide the pulsed beam of accelerated electrons from the second triplet 646 to the fourth turning magnet 636. The fourth turning magnet 636 is adapted to turn a pulsed beam of accelerated electrons emitted by the first and second accelerators 604, 606 (and received via vacuum electron beam guide 652) in a direction toward the fifth turning magnet 638 when an energizing pulse of electrical current is applied thereto (i.e., which may occur continuously or only when a similar energizing pulse of electrical current is applied to the third turning magnet 612).

The fifth turning magnet 638 (also sometimes referred to as a "fifth kicker magnet 638") is, typically, located in a second auxiliary room 654 substantially beneath the inspection room 634 at a position having an elevation substantially equal to the elevation of the position of the fourth turning magnet 636. Third and fourth triplets 656, 658 (e.g., sets of focusing lenses) are interposed between the fourth and fifth turning magnets 636, 638 to refocus the pulsed beams of accelerated electrons emitted by the first and second accelerators 604, 606. The third triplet 656 is connected to the fourth turning magnet 636 by a vacuum electron beam guide 660 which is adapted to guide the pulsed beam of accelerated electrons from the fourth turning magnet 638 to the input of the third triplet 656. A vacuum electron beam guide 662 is connected to the output of the third triplet 656 and to the input of the fourth triplet 658, and is configured to direct a pulsed beam of accelerated electrons from the third triplet 656 to the fourth triplet 658. The output of the fourth triplet 658 is connected to the input of the fifth turning magnet 638 by a vacuum electron beam guide 664 that is adapted to guide the pulsed beam of accelerated electrons from the fourth triplet 658 to the fifth turning magnet 638. The fifth turning magnet 658 is adapted to turn a pulsed beam of accelerated electrons emitted by the first or second accelerator 604, 606 (and received via vacuum electron beam guide 664) toward the second conversion target 640 when an energizing pulse of electrical current is applied thereto (i.e., which may occur continuously or only when a similar energizing pulse of electrical current is applied to the third and fourth turning magnets 612, 636, 638).

The second conversion target 640 is connected to the fifth turning magnet 638 by a vacuum electron beam guide 666 extending therebetween that is adapted to guide pulses of electrons of a pulsed beam of accelerated electrons toward the second conversion target 640. The second conversion target 640 is operable to receive pulses of electrons of a pulsed beam of accelerated electrons from vacuum electron beam guide 666 and to convert the received pulses of electrons into a third pulsed bremsstrahlung (or x-ray) beam 668 that is output from the second conversion target 640 and directed toward a second collimator 670. Generally, the third pulsed bremsstrahlung beam 668 includes first and second energy spectra corresponding to the first and second energy levels of the pulses of electrons that are present in a pulsed beam of accelerated electrons emitted by the first or second accelerators 604, 606.

The second collimator 670, typically, includes an elongate, narrow opening (e.g., a slot) through which a portion of the third pulsed bremsstrahlung beam 668 passes to produce a fourth pulsed bremsstrahlung beam 672 having a beam shape suitable for cargo container inspection. Preferably, the fourth pulsed bremsstrahlung beam 672 has a fan shape upon exiting the second collimator 670. The second collimator 670 is, generally, mounted to and/or integrated into a wall 674 separating the second auxiliary room 654 in which the fifth turning magnet 638 and second conversion target 640 reside and the inspection room 634 through which cargo containers 602 are moved and exposed to the fourth pulsed bremsstrahlung beam 672 exiting the second collimator 670. During inspection, the cargo containers 602 are, generally, moved by a conveyor 676 in a linear direction of travel that is perpendicular to a vertical axis 678 extending through the second conversion target 640 such that the fourth pulsed bremsstrahlung beam 672 is directed predominantly at and impinges on the bottom of each cargo container 602 during movement thereof through the inspection room 634.

The non-intrusive inspection system 600 additionally comprises a detector system 678 having a detector array 680 with a plurality of detectors 682 that are each operable to receive a portion of the second and fourth pulsed bremsstrahlung beams 628, 672 after they pass through a larger container 602 and produce electrical signals representative thereof. The detector array 680, generally, has an "L" shape with a first portion 684 thereof being oriented in a substantially vertical plane perpendicular to the longitudinal axis 627 of the first accelerator 604 and substantially adjacent a side of a cargo container 602 as the cargo container 602 travels through the inspection room 634. The detector array 680 also has a second portion 686 that is oriented in a substantially horizontal plane perpendicular to the substantially vertical plane of the first portion 684 thereof and perpendicular to the vertical axis 678 extending through the second conversion target 640 such that the second portion 686 of the detector array 680 extends at least partially above a cargo container 602 as the cargo container 602 travels through the inspection room 634.

In order to enable the reception of portions of the second pulsed bremsstrahlung beam 628 that may pass through the top, or roof, of a cargo container 602, some of the individual detectors 682 of the second portion 686 of the detector array 680 are slightly turned in a direction somewhat toward, or facing, the first collimator 622 as opposed to being oriented entirely in a downward direction perpendicular to the horizontal plane of the second portion 686 of the detector array 680. Similarly, in order to enable the reception of portions of the fourth pulsed bremsstrahlung beam 672 that may pass through a side of a cargo container 602, some of the individual detectors 682 of the first portion 684 of the detector array 680 are slightly turned in a direction somewhat toward, or facing, the second collimator 670 as opposed to being oriented entirely in a direction perpendicular to the vertical plane of the first portion 684 of the detector array 680. It should be noted that because the non-intrusive inspection system 600 exposes a cargo container 602 to two pulsed bremsstrahlung beams 628, 672 and has a detector array 680 that is fully populated with detectors 682 for detection and imaging capability in two planes (i.e., the vertical plane of the first portion 684 of the detector array 680 and the horizontal plane of the second portion 686 of the detector array 680), the non-intrusive inspection system 600 of the sixth exemplary embodiment is, typically, categorized as a "dual-plane inspection system".

Although not described in detail herein, the non-intrusive inspection system 600 further comprises various other components, including an imaging subsystem having data communication equipment and computer systems with appropriate software, that are configured to receive and transform electrical signals produced by the detector array 680 into images of the contents of a cargo container 602 for display to inspection system operators. The images produced by the imaging subsystem, generally, comprise two-dimensional views of the contents of a cargo container 602 taken for the first view from the perspective of a side thereof such that a first image may extend between the container's ends and the container's top and bottom, and taken for the second view from the perspective of the bottom thereof such that a second image may extend between the container's ends and the container's sides.

The non-intrusive inspection system 600 further comprises a material discrimination subsystem that is connected to and receives electrical signals from the detector array 680, and that identifies, or discriminates, various materials present in the contents of a cargo container 602. Such material discrimination is possible because the non-intrusive inspection system 600 utilizes two accelerators 604, 606 that produce pulsed beams of accelerated electrons having first and second energy levels and exposes a cargo container 602 to pulsed bremsstrahlung beams 628, 672 each having first and second energy spectra (i.e., due to the creation of the pulsed bremsstrahlung beams 628, 672 from the pulsed beams of electrons having first and second energy levels). The material discrimination subsystem is operable to receive data corresponding to the x-ray pulses that pass through the opposing sides and top and bottom of a cargo container 602 in the form of electrical signals received from the detector array 680. The material discrimination subsystem is further operable to analyze the received data and, using methods known to one of ordinary skill in the art, to identify and/or discriminate the materials present in the contents of a cargo container 602.

Figure 17:
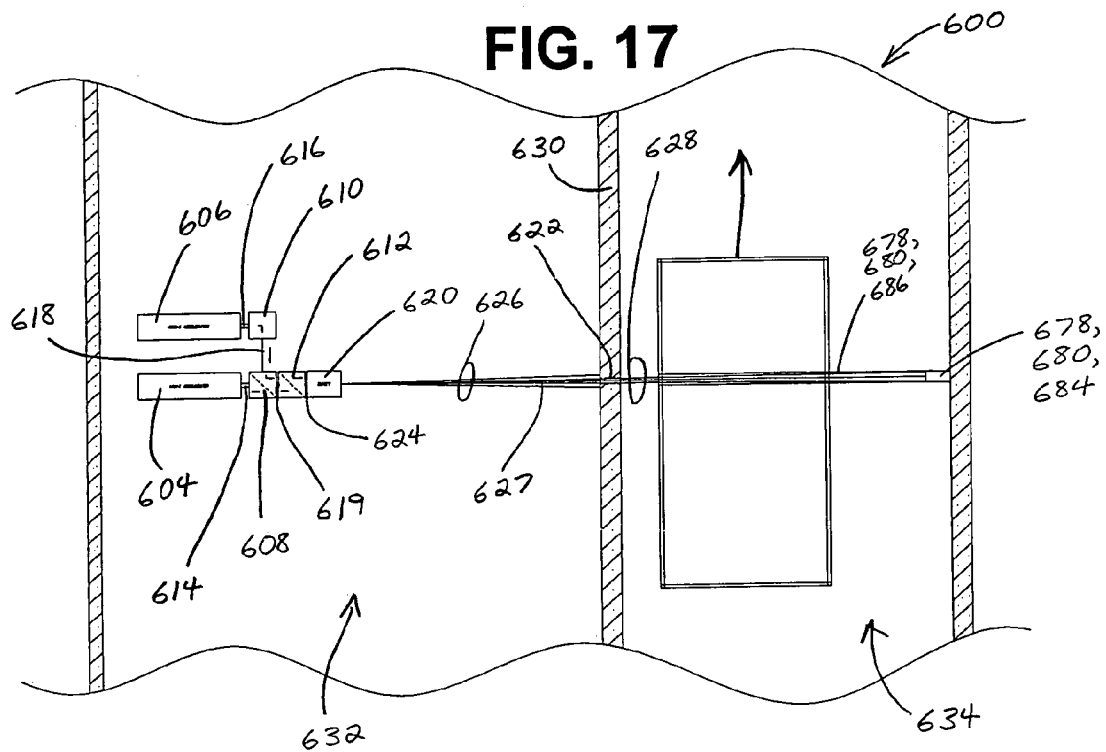
FIG. 17 displays a top plan, schematic sectional view of the non-intrusive inspection system of FIG. 16 in accordance with the sixth exemplary embodiment of the present invention.

FIG. 17 displays a top plan, schematic sectional view of the non-intrusive inspection system 600 of FIG. 16 in accordance with the sixth exemplary embodiment of the present invention. As seen in FIG. 17, the first and second accelerators 604, 606 are positioned in a substantially side-by-side arrangement such that the directions of the pulsed beams of accelerated electrons emitted by the first and second accelerators 604, 606 are in respective first and second directions that are substantially parallel. Similarly, the first and second turning magnets 608, 610 are also positioned in a substantially side-by-side arrangement. The third turning magnet 612 is positioned adjacent the first turning magnet 608 along the first accelerator's longitudinal axis 627 between the first turning magnet 608 and the first conversion target 640.

In operation, the first and second accelerators 604, 606 and the first, second and third turning magnets 608, 610, 612 of the non-intrusive inspection system 600 are appropriately controlled to produce a pulsed beam of accelerated electrons with odd numbered pairs of consecutive pulses of electrons thereof being directed toward the first conversion target 620 and even numbered pairs of consecutive pulses of electrons thereof being directed toward the second conversion target 640. Each pair of electron pulses of the pulsed beam of accelerated electrons includes a first pulse from the first accelerator 604 having a first energy level and a second pulse from the second accelerator 606 having a second energy level. The first and second energy levels are, generally, different. As a consequence, the first and third pulsed bremsstrahlung beams 626, 668 generated by the first and second conversion targets 620, 640 each include different first and second energy spectra. Because two pulsed bremsstrahlung beams 628, 672 are employed with a detector array 680 capable of detecting portions of the pulsed bremsstrahlung beams 628, 672, in horizontal and vertical planes, that pass through a cargo container 602, the non-intrusive inspection system 600 produces two-dimensional views of the cargo container 602 from different directions that, essentially, allow three-dimensional viewing of the contents of the cargo container 602. Further, because the two pulsed bremsstrahlung beams 628, 672 each have first and second energy spectra corresponding to the first and second energy levels of the pulses of electrons produced by the first and second accelerators 604, 606, the non-intrusive inspection system 600 can distinguish between and identify materials present in the contents of, or objects in, a cargo container 602.

More specifically, at a first time of a first pair of times, the first accelerator 604 is operated to generate a pulse of electrons having a first energy level that is directed to the first turning magnet 608 by vacuum electron beam guide 614. Concurrently, no energizing pulses are applied to the first turning magnet 608 or the third turning magnet 612, thereby placing the first and third turning magnets 608, 612 into a de-energized state and allowing the pulse of electrons from the first accelerator 604 to pass non-redirected through the first and third turning magnets 608, 612 and on toward the first conversion target 620. Upon receiving the pulse of electrons having a first energy level produced by the first accelerator 604 at the first time of the first pair of times, the first conversion target 620 converts the received pulse of electrons into a pulse of bremsstrahlung (i.e., a pulse of first bremsstrahlung beam 626) having a first energy spectra corresponding to the first energy level of the pulse of electrons from the first accelerator 604. The produced pulse of bremsstrahlung is emitted from the first conversion target 620 in a direction toward the first collimator 622 which shapes the pulse of bremsstrahlung to produce a shaped pulse of bremsstrahlung (i.e., a pulse of second bremsstrahlung beam 628) which impinges upon a side of a cargo container 602 being moved through the inspection room 634.

At a second time subsequent to the first time of the first pair of times, the second accelerator 606 is operated to generate a pulse of electrons having a second energy level that is guided to the second turning magnet 610 by vacuum electron beam guide 616. Concurrently, energizing pulses are applied to the first and second turning magnets 608, 610, thereby placing the first and second turning magnets 608, 610 into energized states. When so energized, the second turning magnet 610 receives the pulse of electrons from the second accelerator 606 and turns, or directs, it in a direction toward the first turning magnet 608 via vacuum electron beam guide 618. The first turning magnet 608, when so energized, receives the pulse of electrons from the second accelerator 606 and turns, or directs, it in a new direction toward the third turning magnet 612 through vacuum electron beam guide 619. No energizing pulse is applied to the third turning magnet 612, thereby maintaining the third turning magnet 612 in a de-energized state and allowing the pulse of electrons from the second accelerator 606 to pass through the third turning magnet 612 in an non-redirected manner and on toward the first conversion target 620. Upon receiving the pulse of electrons having a second energy level produced by the second accelerator 606 at the second time of the first pair of times, the first conversion target 620 converts the received pulse of electrons into a pulse of bremsstrahlung (i.e., a pulse of first bremsstrahlung beam 626) having second spectra corresponding to the second energy level of the pulse of electrons from the second accelerator 604. The produced pulse of bremsstrahlung (or x-rays) is emitted from the first conversion target 620 in a direction toward the first collimator 622 which shapes the pulse of bremsstrahlung to produce a shaped pulse of bremsstrahlung (i.e., a pulse of second bremsstrahlung beam 628) which impinges upon a side of a cargo container 602 being moved through the inspection room 634.

At a first time of a second pair of times, the first accelerator 604 is operated to generate a pulse of electrons having a first energy level that is directed to the first turning magnet 608 by vacuum electron beam guide 614. Concurrently, no energizing pulse is applied to the first turning magnet 608, thereby placing the first turning magnet 608 into a de-energized state and allowing the pulse of electrons from the first accelerator 604 to pass through the first turning magnets 608 non-redirected and on to the third turning magnet 612. Still concurrently, an energizing pulse is applied to the third, fourth, and fifth turning magnets 612, 636, 638, thereby placing the third, fourth, and fifth turning magnets 612, 636, 638 into energized states. When so energized, the third turning magnet 612 receives the pulse of electrons from the first accelerator 604 (i.e., via the first turning magnet 608) and turns, or directs, it in a new direction toward the fourth turning magnet 636 via vacuum electron beam guide 648. After being turned by the third turning magnet 612, the pulse of electrons from the first accelerator 604 travels through the first and second triplets 644, 646 and vacuum electron beam guides 648, 650, 652 to the fourth turning magnet 636. While traveling through the first and second triplets 644, 646, the pulse of electrons is re-focused to minimize dispersion of the electrons thereof.

The fourth turning magnet 636 turns, or directs, the pulse of electrons from the first accelerator 604 in a new direction toward the fifth turning magnet 638 via vacuum electron beam guide 660. After being turned by the fourth turning magnet 636, the pulse of electrons from the first accelerator 604 travels through the third and fourth triplets 656, 658 and vacuum electron beam guides 660, 662, 664 to the fifth turning magnet 638. While traveling through the third and fourth triplets 656, 658, the pulse of electrons is re-focused to minimize dispersion of the electrons thereof. Then, the fifth turning magnet 638 turns, or directs, the pulse of electrons from the first accelerator 604 in a new direction toward the second conversion target 640 via vacuum electron beam guide 666. Upon receiving the pulse of electrons having a first energy level produced by the first accelerator 604 at the first time of the second pair of times, the second conversion target 640 converts the received pulse of electrons into a pulse of bremsstrahlung (i.e., a pulse of third bremsstrahlung beam 668) having first spectra corresponding to the first energy level of the pulse of electrons from the first accelerator 604. The produced pulse of bremsstrahlung is emitted from the second conversion target 640 in a direction toward the second collimator 670 which shapes the pulse of bremsstrahlung to produce a shaped pulse of bremsstrahlung (i.e., a pulse of fourth bremsstrahlung beam 672) which impinges upon a bottom of a cargo container 602 being moved through the inspection room 634.

At a second time of a second pair of times, the second accelerator 604 is operated to generate a pulse of electrons having a second energy level that is directed to the second turning magnet 610 by vacuum electron beam guide 616. Concurrently, energizing pulses are applied to the first and second turning magnets 608, 610, thereby placing the first and second turning magnets 608, 610 into energized states. When so energized, the second turning magnet 610 receives the pulse of electrons from the second accelerator 606 and turns, or directs, it in a new direction toward the first turning magnet 608 via vacuum electron beam guide 618. The first turning magnet 608, when so energized, receives the pulse of electrons from the second accelerator 606 and turns, or directs, it in a new direction toward the third turning magnet 612 through vacuum electron beam guide 619. Still concurrently, an energizing pulse is applied to the third, fourth, and fifth turning magnets 612, 636, 638, thereby placing the third, fourth, and fifth turning magnets 612, 636, 638 into energized states. When so energized, the third turning magnet 612 receives the pulse of electrons from the second accelerator 606 (i.e., via the first and second turning magnets 608, 610) and turns, or directs, it in a new direction toward the fourth turning magnet 636 via vacuum electron beam guide 648. After being turned by the third turning magnet 612, the pulse of electrons from the second accelerator 606 travels through the first and second triplets 644, 646 and vacuum electron beam guides 648, 650, 652 to the fourth turning magnet 636. While traveling through the first and second triplets 644, 646, the pulse of electrons is re-focused to minimize dispersion of the electrons thereof.

The fourth turning magnet 636 turns, or directs, the pulse of electrons from the second accelerator 606 in a new direction toward the fifth turning magnet 638 via vacuum electron beam guide 660. After being turned by the fourth turning magnet 636, the pulse of electrons from the second accelerator 606 travels through the third and fourth triplets 656, 658 and vacuum electron beam guides 660, 662, 664 to the fifth turning magnet 638. While traveling through the third and fourth triplets 656, 658, the pulse of electrons is re-focused to minimize dispersion of the electrons thereof. Then, the fifth turning magnet 638 turns, or directs, the pulse of electrons from the second accelerator 606 in a new direction toward the second conversion target 640 via vacuum electron beam guide 666. Upon receiving the pulse of electrons having a second energy level produced by the second accelerator 606 at the second time of the second pair of times, the second conversion target 640 converts the received pulse of electrons into a pulse of bremsstrahlung (i.e., a pulse of third bremsstrahlung beam 668) having second spectra corresponding to the second energy level of the pulse of electrons from the second accelerator 606. The produced pulse of bremsstrahlung (or x-rays) is emitted from the second conversion target 640 in a direction toward the second collimator 670 which shapes the pulse of bremsstrahlung to produce a shaped pulse of bremsstrahlung (i.e., a pulse of fourth bremsstrahlung beam 672) which impinges upon a bottom of a cargo container 602 being moved through the inspection room 634.

Operation of the first and second accelerators 604, 606 and the first, second, third, fourth and fifth turning magnets 608, 610, 612, 636, 638 continues in a similar manner during operation of the non-intrusive inspection system 600 to direct odd numbered pairs of pulses of electrons produced by the first and second accelerators 604, 606 toward the first conversion target 620 and even numbered pairs of pulses of electrons produced by the first and second accelerators 604, 606 toward the second conversion target 640. The second and fourth pulsed bremsstrahlung beams 628, 672 produced therefrom, as a consequence, comprise pairs of pulses of bremsstrahlung that impinge, respectively, upon a side, or wall, and bottom of a cargo container 604 at alternating times, thereby causing the detectors 682 of the detector array 680 to alternately produce electrical signals representative of the portions of the pairs of pulses of bremsstrahlung that pass through the contents of a cargo container 602 from a side or bottom thereof and strike the detectors 682: The detector system 680 communicates the produced electrical signals, or an equivalent thereof, to the imaging subsystem for the generation of respective two-dimensional images representative of the contents of (or, objects present within) the cargo container 602 when viewed from a side and bottom thereof.

Figure 18:
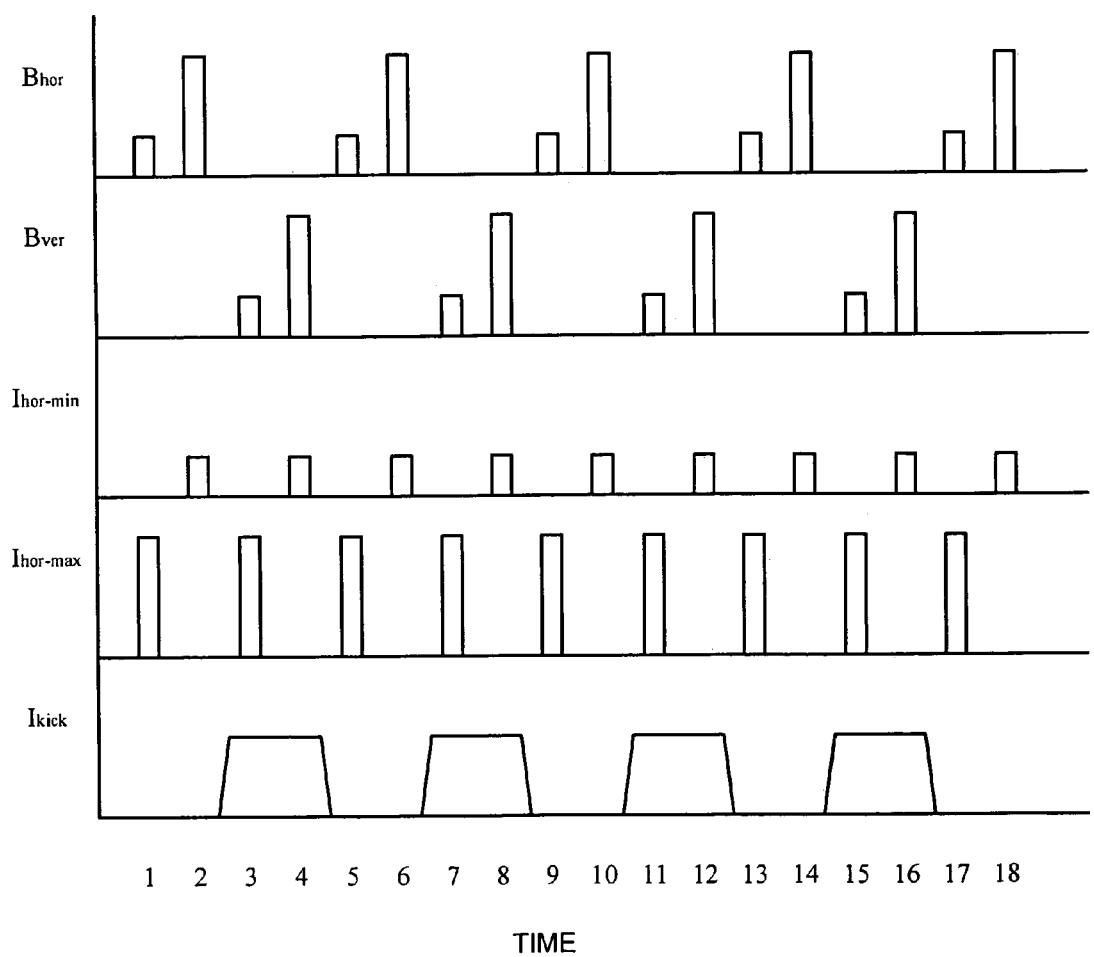
FIG. 18 displays a timing diagram illustrating the timing of various pulses during operation of the non-intrusive inspection system of FIG. 16 in accordance with the sixth exemplary embodiment of the present invention.

FIG. 18 displays a timing diagram illustrating the relative timing of the pairs of electron beam current pulses of the pulsed beams of accelerated electrons alternatingly impinging on the first and second conversion targets 620, 640, the alternating bremsstrahlung pulses of the second and fourth pulsed bremsstrahlung beams 628, 672, and the energizing signal applied to the third turning magnet 612, in accordance with the sixth exemplary embodiment of the present invention. As illustrated in FIG. 18, at a first pair of times denoted by the numbers "1" and "2" on the horizontal time axis of the timing diagram, no energizing signal (i.e., electrical current) is applied to the third turning magnet 612 as indicated by the magnet current, $I_{kick}$, having a zero value. At the first pair of times and by virtue of no energizing signal being applied to the third turning magnet 612, the first and second accelerators 604, 606 emit a pair of electron beam current pulses (i.e., one electron beam current pulse being from each accelerator 604, 606) that pass through the third turning magnet 612 without being turned. Therefore, at the first pair of times, the electron beam current pulses (i.e., denoted by electron beam current pulses $I_{hor-max}$ and $I_{hor-min}$) emitted from the first and second accelerators 604, 606 impinge on the first conversion target 620, causing the generation of pulses of bremsstrahlung of the first and second pulsed bremsstrahlung beams 626, 628 having first and second energy spectra (i.e., denoted by a pair of pulses on the $B_{hor}$ axis) corresponding to the first and second energy levels of the electron beam current pulses.

At a second pair of times denoted by the numbers "3" and "4" on the horizontal time axis of the timing diagram, an energizing signal (i.e., current) is applied to the third turning magnet 612 as indicated by the magnet current, $I_{kick}$, having a non-zero value. At the second pair of times and by virtue of an energizing signal being applied to the third turning magnet 612, the first and second accelerators 604, 606 emit a pair of electron beam current pulses (i.e., one electron beam current pulse being from each accelerator 604, 606) that are turned by the third turning magnet 612 toward the fourth turning magnet 636. Therefore, at the second pair of times, the electron beam current pulses emitted from the first and second accelerators 604, 606 impinge on the second conversion target 640, causing the generation of pulses of bremsstrahlung of the third and fourth pulsed bremsstrahlung beams 668, 672 having first and second energy spectra (i.e., denoted by the pair of pulses on the $B_{ver}$ axis) corresponding to the first and second energy levels of the electron beam current pulses. As additionally illustrated in FIG. 18, the timing of, pulses at the first and second pairs of times is repeated at respectively successive alternating pairs of times with the beam currents and energy spectra corresponding to the first pair of times being repeated at successive odd numbered pairs of times and the beam currents and energy spectra corresponding to the second pair of times being repeated at successive even numbered pairs of times.

It should be noted that although the non-intrusive inspection systems of certain embodiments have been described with accelerators, turning magnets, conversion targets, and/or collimators located above an inspection room, the scope of the present invention encompasses similar non-intrusive inspection systems in which the respective accelerators, turning magnets, conversion targets, and/or collimators are located below an inspection room such that the predominant portion of a pulsed bremsstrahlung beam produced thereby passes initially through the bottom of a cargo container. Conversely, it should be noted that although the non-intrusive inspection systems of certain embodiments have been described with accelerators, turning magnets, conversion targets, and/or collimators located below an inspection room, the scope of the present invention encompasses similar non-intrusive inspection systems in which the respective accelerators, turning magnets, conversion targets, and/or collimators are located above an inspection room such that the predominant portion of a pulsed bremsstrahlung beam produced thereby passes initially through the top of a cargo container. Still further, it should be noted that although the pulses of electrons, corresponding pulses of bremsstrahlung (or x-rays), and turning magnet signal pulses have been described herein with respect to some embodiments as having a particular sequence in time, it should be understood that the scope of the present invention encompasses all possible sequences or orders in time of such pulses.

While the exemplary embodiments described herein contemplate that the components of the non-intrusive inspection systems of the present invention are to be installed in building-like structures, it should be understood that the scope of the present invention includes and contemplates positioning the components of the non-intrusive inspection systems of the present invention on mobile platforms so that they may be moved from location to location where needed for screening and inspection of cargo containers or other articles. For example and not limitation, the non-intrusive inspection system 200 of the second exemplary embodiment may be implemented and arranged with the first and second accelerators 204, 206, conversion target 206, and collimator 216 residing in a trailer of a movable first tractor-trailer truck. The detection system 226 and detector array 228 may reside in a trailer of a movable second tractor-trailer truck that is backed-up to the rear of the trailer of the first tractor-trailer truck leaving enough space therebetween for a movable conveyor (i.e., for moving cargo containers through the second pulsed bremsstrahlung beam 218) to be positioned such that the longitudinal axis of the movable conveyor is perpendicular to the longitudinal axis 236 of the first accelerator 204. In such an implementation or arrangement, the first portion 232 of the detector array 228 is also positioned perpendicular to the longitudinal axis 236 of the first accelerator 204.

Whereas the present invention has been described in detail above with respect to exemplary embodiments thereof, it is understood that variations and modifications can be effected within the spirit and scope of the invention, as described herein before and as defined in the appended claims.

What is claimed is:

1. An apparatus for inspecting the contents of a container employed in the transportation industry, said apparatus comprising:
   a first accelerator for producing a first beam of electron pulses having a first energy level and traveling predominantly in a first direction;
   a second accelerator for producing a second beam of electron pulses having a second energy level and traveling predominantly in a second direction different from said first direction;
   at least one turning device for redirecting said second beam of electron pulses to travel substantially in said first direction; and
   a conversion target for receiving said first and second beams of electron pulses and for producing a radiation beam for inspecting contents of a container.

2. The apparatus of claim 1, wherein said at least one turning device is adapted to redirect said second beam of electron pulses to travel substantially collinear with said first beam of electron pulses.

3. The apparatus of claim 1, wherein said first energy level and said second energy level are different.

4. The apparatus of claim 1, wherein said radiation beam comprises first pulses of radiation having first spectra corresponding to said first energy level and second pulses of radiation having second spectra corresponding to said second energy level.

5. The apparatus of claim 4, wherein said first pulses of radiation and said second pulses of radiation are alternately positioned within said radiation beam.

6. The apparatus of claim 1, wherein said at least one turning device is interposed between said first beam of electron pulses and said second beam of electron pulses and is operable to select between said first beam of electron pulses and said second beam of electron pulses.

7. The apparatus of claim 1, wherein said at least one turning device comprises a first turning device for receiving said first beam of electron pulses and said second beam of electron pulses, for selectively emitting one of said first beam of electron pulses and said second beam of electron pulses, and for selectively redirecting said second beam of electron pulses to travel substantially in said first direction, and a second turning device for receiving said second beam of electron pulses and redirecting said second beam of electron pulses toward said first turning device.

8. The apparatus of claim 1, wherein said radiation beam for inspecting contents of a container is adapted for performing discrimination of materials present in said contents of said container.

9. An apparatus for inspecting the contents of a container employed in the transportation industry, said apparatus comprising:
   a first accelerator for producing a first beam of electron pulses having a first energy level and propagating predominantly in a first direction;
   a second accelerator for producing a second beam of electron pulses having a second energy level and propagating predominantly in a second direction different from said first direction; and
   a conversion target for receiving said first and second beams of electrons and for producing a radiation beam for inspecting contents of a container;
   wherein said first beam of electron pulses and said second beam of electron pulses define an acute angle therebetween.

10. The apparatus of claim 9, wherein said first energy level and said second energy level are different.

11. The apparatus of claim 9, wherein said radiation beam comprises first pulses of radiation having first spectra corresponding to said first energy level and second pulses of radiation having second spectra corresponding to said second energy level.

12. The apparatus of claim 11, wherein radiation pulses of said first pulses of radiation and radiation pulses of said second pulses of radiation are alternately positioned within said radiation beam.

13. The apparatus of claim 9, wherein said acute angle has measure between zero degrees and forty-five degrees.

14. An apparatus for inspecting the contents of a container employed in the transportation industry, said apparatus comprising:
   an accelerator for producing a beam of electron pulses traveling predominantly in a first direction;
   a turning device for receiving said beam of electron pulses from said accelerator and for selectively allowing said beam of electron pulses to continue traveling predominantly in said first direction or redirecting said beam of electron pulses to travel predominantly in a second direction different from said first direction;
   a first conversion target for receiving said beam of electron pulses when said beam of electron pulses is traveling predominantly in said first direction and for producing a first radiation beam for inspecting contents of a container with respect to a first plane; and
   a second conversion target for receiving said beam of electrons when said beam of electrons has been redirected by said turning device and for producing a second radiation beam for inspecting said contents of said container with respect to a second plane.

15. The apparatus of claim 14, wherein said first plane is substantially perpendicular to said second plane.

16. The apparatus of claim 14, wherein at least one of said first conversion target and said second conversion target is located substantially beneath said container during inspection of said container.

17. The apparatus of claim 14, wherein said first plane comprises a plane substantially parallel to a side of said container and said second plane comprises a plane substantially parallel to a bottom of said container.

18. The apparatus of claim 14, wherein said beam of electron pulses comprises a first plurality of electron pulses having a first energy level and a second plurality of electron pulses having a second energy level different from said first energy level.

19. The apparatus of claim 14, wherein said accelerator is configured to produce said beam of electron pulses comprising a first plurality of electron pulses having a first energy level and a second plurality of electron pulses having a second energy level different from said first energy level.

20. The apparatus of claim 14, wherein at least one of said first and second radiation beams comprises first pulses of radiation having first spectra and second pulses of radiation having second spectra different from said first spectra.

21. The apparatus of claim 14, wherein at least one of said first and second radiation beams is adapted for performing discrimination of materials present in said contents of said container.

22. The apparatus of claim 14, wherein at least one of said first and second radiation beams is adapted for generating an image of said contents of said container.

23. The apparatus of claim 14, wherein said accelerator comprises a first accelerator and said beam of electron pulses comprises a first beam of electron pulses having a first energy level, and wherein said apparatus further comprises a second accelerator for producing a second beam of electron pulses having a second energy level different from said first energy level.

24. The apparatus of claim 23, wherein said turning device comprises a first turning device, and wherein said apparatus further comprises a second turning device for receiving said first and second beams of electron pulses and for selectively mixing electron pulses of said second beam of electron pulses with electron pulse of said first beam of electron pulses.

25. The apparatus of claim 23, wherein said first radiation beam comprises first pulses of radiation having first spectra corresponding to said first energy level and second spectra corresponding to said second energy level, and wherein said second radiation beam comprises first pulses of radiation having first spectra corresponding to said first energy level and second spectra corresponding to said second energy level.

26. An apparatus for inspecting the contents of a container employed in the transportation industry, said apparatus comprising:

a first accelerator for producing a first beam of electron pulses comprising a first plurality of electron pulses having a first energy level and a second plurality of electron pulses having a second energy level different from said first energy level;

a second accelerator for producing a second beam of electron pulses comprising a first plurality of electron pulses having a first energy level and a second plurality of electron pulses having a second energy level different from said first energy level;

a first conversion target for receiving said first beam of electron pulses and for producing a first radiation beam for generating first data related to contents of said container with respect to a first plane; and a second conversion target for receiving said second beam of electron pulses and for producing a second radiation beam for generating second data related to said contents of said container with respect to a second plane.

27. The apparatus of claim 26, wherein said first plane is substantially perpendicular to said second plane.

28. The apparatus of claim 26, wherein at least one of said first radiation beam and said second radiation beam comprise first spectra corresponding to said first energy level and second spectra corresponding to said second energy level.

29. The apparatus of claim 26, wherein at least one of said first data and said second data is usable for discriminating materials of said contents of said container.

30. The apparatus of claim 26, wherein said first data and said second data are usable for producing multi-plane images of said contents of said container.

* * * * *